US012636469B2

(12) United States Patent
Albertsen et al.

(10) Patent No.: US 12,636,469 B2
(45) Date of Patent: May 26, 2026

(54) INTRAVENOUS TUBING SECUREMENT BAND WITH ADJUSTABLE OVERALL LENGTH

(71) Applicant: Quest Medical, Inc., Allen, TX (US)

(72) Inventors: Jeff J. Albertsen, McKinney, TX (US); Joel Fontenot, Dallas, TX (US)

(73) Assignee: Quest Medical, Inc., Allen, TX (US)

( * ) Notice: Subject to any disclaimer, the term of this patent is extended or adjusted under 35 U.S.C. 154(b) by 861 days.

(21) Appl. No.: 17/988,864

(22) Filed: Nov. 17, 2022

(65) Prior Publication Data

US 2023/0149665 A1 May 18, 2023

Related U.S. Application Data

(60) Provisional application No. 63/384,063, filed on Nov. 16, 2022, provisional application No. 63/280,227, filed on Nov. 17, 2021.

(51) Int. Cl.
A61M 25/02 (2006.01)

(52) U.S. Cl.
CPC ..... A61M 25/02 (2013.01); A61M 2025/0253 (2013.01)

(58) Field of Classification Search
CPC .......... A61M 25/02; A61M 2025/0253; A61M 2025/0206; A61M 2025/026; B65D 63/1027; F16L 3/233; F16L 3/2334; F16L 3/2336
See application file for complete search history.

(56) References Cited

U.S. PATENT DOCUMENTS

| | | | |
|---|---|---|---|
| 1,810,027 A | 6/1931 | Moran et al. |
| 2,961,785 A | 11/1960 | Toepfer |
| 3,147,522 A | 9/1964 | Schumm |
| 3,255,501 A | 6/1966 | Maxime |
| 3,438,095 A | 4/1969 | Evans |
| 3,875,620 A | 4/1975 | Wells et al. |

(Continued)

FOREIGN PATENT DOCUMENTS

| | | |
|---|---|---|
| CA | 692631 A | 8/1964 |
| CN | 104648811 A | 5/2015 |

(Continued)

OTHER PUBLICATIONS

United States Patent Office, Notice of Allowance dated Sep. 20, 2023 in U.S. Appl. No. 17/151,287 (6 pages).

(Continued)

*Primary Examiner* — Brian P Wolcott
(74) *Attorney, Agent, or Firm* — Trop, Pruner & Hu, P.C.

(57) ABSTRACT

An embodiment provides an adjustable intravenous (IV) securement band with non-occlusive retention in case of excessive force (i.e., automatically loosens) and traction for securing an IV to a patient's arm. Embodiments may further include features such as guides and or channels on the band to hold tubing. Embodiments may be secured to patients to be used as a non-adhesive securement aid for tubing/catheter (e.g., IV's, enteral tubes, Foley catheters, endotracheal tubes, nasogastric (NG) tubes, chest tubes, and the like) retention on patients. An embodiment includes a series of separable flaps, any of which may be separated from the band to adjust the length of the band.

20 Claims, 11 Drawing Sheets

(56) References Cited

U.S. PATENT DOCUMENTS

| | | | |
|---|---|---|---|
| 3,913,179 A | 10/1975 | Rhee | |
| D237,781 S | 11/1975 | Dwight | |
| 3,922,758 A | 12/1975 | Wiinnenberg et al. | |
| 4,347,648 A | 9/1982 | Dekkers | |
| 4,377,872 A | 3/1983 | Daniell, Jr. | |
| 4,449,975 A | 5/1984 | Perry | |
| 4,477,950 A * | 10/1984 | Cisek | B65D 63/1027 |
| | | | 24/17 AP |
| 4,676,535 A | 6/1987 | Mautner | |
| 4,976,698 A | 12/1990 | Stokley | |
| 5,317,787 A | 6/1994 | Fortsch | |
| 5,342,317 A | 8/1994 | Claywell | |
| 5,377,387 A | 1/1995 | Freed | |
| 5,395,343 A | 3/1995 | Iscovich | |
| 5,396,684 A | 3/1995 | Yocom | |
| 5,402,971 A | 4/1995 | Bower | |
| 5,581,850 A | 12/1996 | Acker | |
| 5,799,376 A * | 9/1998 | Harsley | B65D 63/10 |
| | | | 24/17 AP |
| D451,372 S | 12/2001 | Cedarberg, III | |
| 6,430,783 B1 | 8/2002 | Benoit | |
| 6,935,001 B2 * | 8/2005 | Barriuso | F16L 3/2334 |
| | | | 24/17 AP |
| D510,856 S | 10/2005 | Cheung | |
| 6,962,014 B2 | 11/2005 | Mccabe et al. | |
| D515,408 S | 2/2006 | Cheung | |
| D565,401 S | 4/2008 | Grady et al. | |
| 7,377,013 B2 * | 5/2008 | Cheung | A01G 17/12 |
| | | | 24/30.5 P |
| 7,621,896 B2 | 11/2009 | Rose | |
| 7,704,587 B2 * | 4/2010 | Harsley | B65D 63/1018 |
| | | | 428/134 |
| D619,887 S | 7/2010 | Colton | |
| 8,302,264 B2 | 11/2012 | Shigematsu et al. | |
| D672,230 S | 12/2012 | Laverack et al. | |
| 8,387,215 B2 | 3/2013 | Koncelik, Jr. | |
| 8,709,568 B2 * | 4/2014 | Harsley | B65D 63/1018 |
| | | | 24/17 AP |
| 9,021,665 B2 | 5/2015 | Chen | |
| 9,039,663 B2 | 5/2015 | Bond et al. | |
| D776,272 S | 1/2017 | Backes et al. | |
| 9,895,485 B1 | 2/2018 | McNeill et al. | |
| 10,189,588 B2 * | 1/2019 | Milbrandt | B65B 13/22 |
| D848,615 S | 5/2019 | McNeill et al. | |
| D848,616 S | 5/2019 | McNeill et al. | |
| 10,407,226 B2 * | 9/2019 | Harsley | B65D 63/1027 |
| 10,583,243 B2 | 3/2020 | Burke | |
| 2005/0115028 A1 * | 6/2005 | Cheung | B65D 63/1027 |
| | | | 24/16 PB |
| 2006/0289375 A1 * | 12/2006 | Haschke | A22C 11/12 |
| | | | 211/113 |
| 2008/0276432 A1 | 11/2008 | McNeill | |
| 2014/0046265 A1 | 2/2014 | Kay et al. | |
| 2019/0015636 A1 * | 1/2019 | Robinson | A61M 25/02 |
| 2019/0314611 A1 | 10/2019 | Harders | |
| 2020/0093985 A1 | 3/2020 | Greenberg | |
| 2021/0244917 A1 | 8/2021 | Albertsen et al. | |

FOREIGN PATENT DOCUMENTS

| | | |
|---|---|---|
| DE | 1176561 B | 8/1964 |
| DE | 2524013 A1 | 12/1975 |
| DE | 4007784 A1 | 9/1991 |
| EP | 0295753 B1 | 9/1990 |
| EP | 0389831 B1 | 8/1993 |
| EP | 0922895 B1 | 8/2002 |
| GB | 2519141 B | 10/1936 |
| GB | 1097213 A | 1/1968 |
| GB | 2466224 B | 9/2012 |
| KR | 100937190 B1 | 1/2010 |
| KR | 20100125052 A | 11/2010 |
| WO | 2006121311 A1 | 11/2006 |

OTHER PUBLICATIONS

United States Patent Office, Office Action dated Jul. 14, 2023 in U.S. Appl. No. 17/151,287 (25 pages).

Sonia Pinkney, et al., "Identifying IV Infusions: IV Tubing Organizer Abbreviation," May 2015, 1 page total. (https://www.researchgate.net/figure/Identifying-IV-Infusions-IV-Tubing).

Bay Medical, "IV Line Organizer," Jan. 17, 2020, 2 pages total. (http://bay-medical.com/products/iv-line-organizer.html).

Haynes, et al., "Managing Spaghetti Syndrome in Critical Care With a Novel Device: A Nursing Perspective, Abstract," Dec. 2015, 2 pages total.

Beata Clasp, "Improving the Safety of Medical Tubing Maintenance via the Beata Clasp," Jan. 17, 2020, 3 pages total.

Jay Haynes, et al., "Managing Spaghetti Syndrome in Critical Care With a Novel Device: A Nursing Perspective," CriticalCareNurse vol. 35, No. 6, Dec. 2015, 8 pages total.

Smooth-On, "Durometer Shore Hardness Scale," Jan. 16, 2020, 2 pages total.

Wagner Instruments, "Force Ten FDX, Compact Digital Force Gage," Jan. 16, 2020, 2 pages.

Merriam-Webster, "Definition of monolithic," Jan. 17, 2020, 7 pages total.

Aliexpress, "30/50 Garden Ties: Reusable Plant Support Shrubs Fastener Tree Locking Nylon Plastic Cable Ties Zip Garden Ties," Data Unknown, 13 pages.

Direct Industry, "Polyethylene Cable Tie / Reusable, AST-170," Jun. 14, 2019, 5 pages total.

Newark, "PE (Polyethylene) Cable Ties," Jun. 14, 2019, 3 pages total.

One up Components, "EDC Gear Strap," Oct. 11, 2017, 2 pages total.

Del City, "Reusable Flexible Straps—Green," Jun. 14, 2019, 2 pages total.

* cited by examiner

Long Axis of Band (411)

INTRAVENOUS TUBING SECUREMENT BAND WITH ADJUSTABLE OVERALL LENGTH

CROSS-REFERENCE TO RELATED APPLICATION

This application claims priority to U.S. Provisional Patent Application No. 63/280,227 filed on Nov. 17, 2021 and entitled "Intravenous Tubing Securement Band with Adjustable Overall Length", the content of which is hereby incorporated by reference.

This application claims priority to U.S. Provisional Patent Application No. 63/384,063 filed on Nov. 16, 2022 and entitled "Intravenous Tubing Securement Band with Adjustable Overall Length", the content of which is hereby incorporated by reference.

BACKGROUND

In many medical care facilities patients may have intravenous (IV) bands that can easily become disorganized and tangled, leading to discomfort should the IV tube be inadvertently pulled or pushed, confusion for medical care providers, and/or a physical hazard that increases the risk for falls for both medical care providers and patients.

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

FIG. 12 shows an embodiment including a series of separable flaps, any of which may be separated from the IV band to adjust the length of the IV band.

DETAILED DESCRIPTION

Figure 1A:
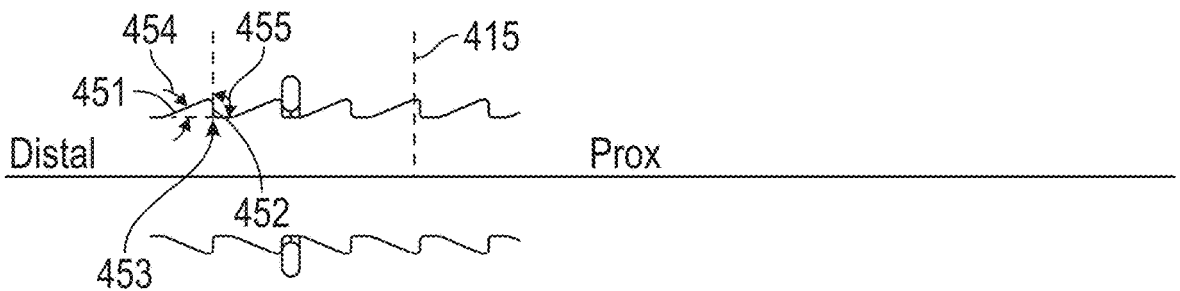
FIG. 1A includes a partial cross-sectional view of a band clinched into a loop.
Figure 1B:
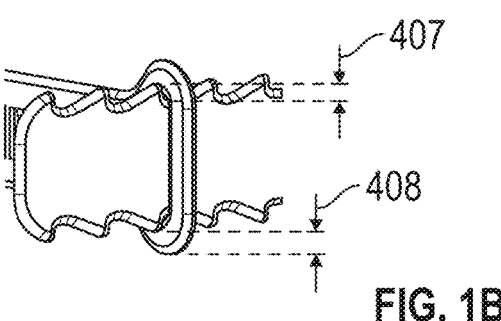
FIG. 1B includes a perspective view of a band clinched into a loop.

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photo, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical contact with each other and "coupled" may indicate elements co-operate or interact with each other, but they may or may not be in direct physical contact. Phrases such as "comprising at least one of A and B" include situations with A, B, or A and B.

The function of an embodiment is to secure IV tubing to a patient's limb (e.g., arm). In an embodiment, the teeth of the IV band are designed to provide some retention of the tubing around the limb, but to "self-adjust" so that the IV band cannot be over-tightened to occlude vessels in the limb or the tube itself. The IV band secures tubing so that IV tubing is retained (remains coupled to the patient) and thereby reduces the risk of IV dislodgement or pull out. Further, the IV band length is adjustable (tear away) to fit a multitude of patient sizes. Also, the IV band has cutout features to allow for breathability and comfort. In addition, the IV band is made of an elastomeric material to provide the "self-adjustment" and tear away functionality An embodiment is a reusable band to be used to aid in the management or securement of tubing lines or electrical cords that become tangled or get in the way of a practicing clinician or nurse. The tubing management band is a soft, flexible strap with a slot for one end to be fed through. The band has teeth along the outer edge (e.g., one or two outer edges depending on the embodiment) that are used to grip the edges of the slot and prevent the band from coming undone. It is adjustable, and has retention that is non-occlusive to tubing.

In various places in a hospital, clinicians require the ability to deliver fluids to a patient through a multitude of tubing lines, or need to use multiple pieces of equipment each with their own cables. As mentioned above, these lines are prone to both tangling and getting snagged on protrusions or tripped over when a patient is moving. To combat this problem, an embodiment of the tubing management band can be used to group a bundle of lines or cables together or to hold them against an IV pole (although other embodiments are designed to focus more on securing an IV tube to a patient). This can reduce the overall length of the line so that it is no longer a trip hazard, or keep it secure in a single place for better clinician access.

Another issue that can arise when delivering fluid to a patient is that a specific line (e.g., therapeutic cable, tube, cord) can be needed and not be readily identified. By securing a line to an IV pole (or bed rail and the like) or wrapping a band around it, it is possible for the clinician to easily and quickly identify the line that they require. An embodiment of the band also does not slide down an IV pole after being tightened so it will remain in place.

An embodiment solves the problem of using tape (or similar solutions) in a hospital environment. The residue that is left behind by tape after it is removed is difficult to clean and can harbor microorganisms that increase infection risk. Since an embodiment of the band has no adhesive, this problem is eradicated or lessened.

In an embodiment, the teeth along the edge of the band in combination with the width of the slot on the band allow for the band to be tightened and remain secure afterwards. The material used to create the band prevents it from sliding down an IV pole when it is tightened.

An embodiment of the band is made from a soft, flexible material to allow for proper functionality (removed more easily and can be stretched for better function).

Various embodiments are used to aid in fluid tubing management, electrical cable management, and the like.

Other alternatives may have teeth and/or slot or slots shaped differently from those embodiments shown in the Figures. Further, the band itself may have a different length, width, and the like from embodiments shown in the Figures.

Embodiments may be used commercially as a replacement to tape, loop and hook fasteners, and the like that are currently used to secure things together in a hospital setting.

An embodiment has no adhesive and leaves no residue when removed. Further, an embodiment may be a monolithic thermoplastic elastomer that is relatively inexpensive and which is easily constructed in high volume with strong reliability.

An embodiment includes a tubing management band that can be used for various things in the hospital including tubing management, securing devices to poles/beds, wrapping electrical cords, and other organizational needs. An embodiment includes a single monolithic piece thermoplastic polymer elastomer (TPE), silicone, and the like that loops around tubing or other objects and threads through the loop on one end to secure it.

An embodiment provides an adjustable band with non-occlusive retention in case of excessive force (i.e., automatically loosens) and traction for the broad use of tubing management in medical device and patient contact applications (e.g., securing an IV band to a patient's arm). Embodiments may further include features such as guides and or channels on the band to hold tubing.

Embodiments may be secured to patients to be used as a non-adhesive securement aid for tubing/catheter (e.g., IV's, enteral tubes, Foley catheters, endotracheal tubes, nasogastric (NG) tubes, chest tubes, and the like) retention on patients. An embodiment may enable organization of tubing orientation for patient comfort. An embodiment includes a rigid plastic connector and/or housing on the band to interface with a catheter surface to achieve coupling of the catheter to the band. An embodiment may couple the connector (rigid or nonrigid) to the band via adhesives.

An embodiment includes a flat sawtooth design that allows the device to remove excess tension to prevent tubing occlusion (e.g., when securing an IV band to a patient's arm). An embodiment contains a special patch that can be used to label the device that can't easily be removed with an alcohol wipe. An embodiment of a band with a smooth surface may allow ink to be easily removed with an alcohol wipe. However, an embodiment of a band with a rough surface may "hide" ink to some extent making removal of all ink with the wipe more difficult.

An embodiment achieves a balance of adequate securement without overtightening which can occlude plastic tubing used is medical devices (which possess a significant risk). However, the size and profile of protuberances in an embodiment achieves this balance. Ease of disengagement of the band during removal (while providing adequate retention) provides for an efficient band. Further, the elastomeric material of the band stretches providing relief to overtightening without loss of circular support integrity (e.g., securing an IV band to a patient's arm). Also, embodiments may be for single patient use or multiuse. Regardless, should a band be contaminated by body or medical fluids, the ability to clean the device is easier without nooks and crannies and otherwise due to simple structures addressed herein.

An embodiment includes protuberances that are not too extremely angled to prevent too strong of a securement which could occlude tubing that the band is securing. Such protuberances also allow for easy adjustability. An embodiment allows the band to be adjusted easily and to not be overtightened and provide some give when the user tries to do so.

Further, a band made with an elastomeric material (of a certain durometer such as Shore A 40) also helps reduce the risk of overtightening and potential occlusions.

An embodiment includes a material with a certain pore size, density or aversion to microbial growth. Pore size and density can be controlled with material selection and changing the pressure at which, for example, injection molding is performed. Further, antimicrobial agents may be added to the material to limit microbial growth.

An embodiment allows for automatic loosening (so as not to overly cinch tubing that may be providing medication to a patient) based on the combination of the material properties (e.g., hardness as measured on Shore durometer scale), shape of the teeth (e.g., shark fin shapes that provide greater resistance to loosening than tightening but still allow for loosening once a force threshold is met), and/or overlap between teeth engaged with the slot and the slot sidewalls (provide greater resistance to loosening than tightening but still allow for loosening once a force threshold is met). Some dimensions are critical in achieving the above performance of greater resistance to loosening than tightening but still allow for loosening once a force threshold is met. In embodiments the dimensions themselves may not be critical so much as the relationship among dimensions (e.g., ratio of overlap between an engaged tooth and a slot sidewall) and the combination of qualities (e.g., hardness of band material in combination with the above-mentioned ratio of overlap between an engaged tooth and a slot sidewall). The above features are useful when securing an IV band to a patient's arm.

Regarding the above criticality, for instance, Applicant determined if the material is too stiff, the teeth will hold too tightly and the band will not loosen itself correctly. If the material is too soft the opposite will occur and the band will loosen too easily. Additionally, because of the material, the slot at the back has the ability to stretch/deflect which aids in relieving tension if a user tries to over tighten the band. The material is not a skin irritant and will not degrade if wiped with an alcohol swab. Materials may include a thermoplastic with a Shore 40A durometer rating. However, other embodiments may use a silicone rubber material. The above features are useful when securing an IV band to a patient's arm.

The shape of the teeth is another critical design feature for function in some embodiments. In at least some embodiments they extend perpendicular (+/−10 degrees) (or at least a portion of the tooth) to the length of band and extend at a length so that the overhang (between tooth and slot sidewall) allows the band to be secured and not immediately come apart. If the teeth extend at particular angles (e.g., angled barbs that slope proximally so that tightening is easy but loosening is difficult) the band holds too tightly. If the overhang of the teeth is more or less, the function would also be impaired.

Thus, embodiments are different from the many, many iterations of zip-ties that would be ineffective for intended uses for embodiments described herein (e.g., a band that is snug enough to hold things but then loosens at a threshold so tubes are not occluded). An embodiment provides the following dimensions for a band 100 (e.g., FIG. 4): (a) Dimensions of hole—0.100" wide (401), 0.65" long (402), (b) Dimensions of teeth—0.095" protrusion from body (403), (c) Dimensions of body to which teeth are formed—0.60" width of body w/o teeth (405), 6.53" overall length (406), 0.08" thickness (404), (d) Material from which band is made—soft flexible plastic such as TPE or a silicone rubber, (e) Dimension between hole and adjacent edge—Overhang (407) of 0.06" from inside of hole to edge of teeth, (f) Width of material around the hole—0.18" (408). While the above measurements address FIG. 4, other embodiments with analogous features (e.g., a slot and teeth) may utilize the same dimensions and/or ratios between dimensions to achieve the above effects (e.g., auto-loosening).

The following examples pertain to further embodiments.

Example 1: A tubing management band comprising: an overall length defined along a long axis of the band; a proximal third, a distal third, and a middle third between the proximal and distal thirds. The band includes a substantially flat first face opposite a substantially flat second face. The band includes a first side wall opposite a second side wall, the first side wall coupling the first and second flat faces to each other and the second side wall also coupling the first and second flat faces to each other. The band includes a distal portion of the first sidewall, the distal portion of the first sidewall including first, second, and third protuberances, and a distal portion of the second sidewall, the distal portion of the second sidewall including fourth, fifth, and sixth protuberances. The band includes a proximal portion of the first sidewall, the proximal portion of the first sidewall including no protuberances, and a proximal portion of the second sidewall, the proximal portion of the second sidewall including no protuberances. The band includes a tip of the first protuberance that extends a first distance, orthogonal to the long axis, from the long axis. The proximal portion of the first sidewall extends a second distance, orthogonal the long axis, from the long axis and the first distance is greater than the second distance. The band includes a slot included in the proximal third of the band and including a first width that is orthogonal to the long axis. The band includes a second width extending orthogonal to the long axis and from the tip of the first protuberance to a tip of the fourth protuberance, wherein the second width is wider than the first width by 0.12 inches. The band includes a third width colinear with the first width and extending from the first side wall to the second sidewall, wherein the third width is wider than the second width by 0.36 inches. The band includes a resilient material. The first protuberance includes a leading edge that slopes away from the long axis as the leading edge extends proximally. The first protuberance includes a trailing edge that meets the first sidewall via an arcuate edge and slopes away from the long axis as the trailing edge extends distally. The leading edge is longer than the trailing edge; (d) the leading edge has a first angle of incidence with the first sidewall, the trailing edge has a second angle of incidence with the first sidewall, and the first angle of incidence is less than the second angle of incidence. The proximal third extends along the long axis and is proximal to the slot by 0.18 inches (463). The slot has a width (401) taken along the long (long) axis of 0.1 inches. The slot has a length (402) (sometimes referred to as a width) taken orthogonal to the long axis of 0.65 inches. The first protuberance extends orthogonal to the long axis and away from the first sidewall by 0.095 inches (407). The band is monolithic and formed from a single structure with no fusions, welds, or adhesions between different sub-portions of the first band.

For example, see first width 402, second width 418, third width 419. For example, the first distance 461 is greater than second distance 462 with regard to axis 411. For example, see leading edge 451, trailing edge 452, arcuate edge 453, first angle of incidence 454, second angle of incidence 455. In an embodiment, the angle 455 may be 90 degrees. However, in other embodiments the angle may be greater than 90 degrees (more open, such as FIG. 8) to make automatic loosening (to avoid cinching a banded tube) easier.

Other embodiments may provide at least one of: (a) the second width is wider than the first width by 0.08, 0.09, 0.11, 0.13, 0.14, 0.15 inches; (b) the third width is wider than the second width by 0.30, 0.31, 0.32, 0.33, 0.34, 0.35, 0.37, 0.38, 0.39, 0.40 inches; (c) the proximal third extends along the long axis and proximal to the slot by 0.14, 0.15, 0.16, 0.17, 0.19, 0.20, 0.21, 0.22, 0.23 inches; (d) the slot has a width taken along the long axis of 0.06, 0.07, 0.08, 0.09, 0.10, 0.11, 0.12, 0.13, 0.14 inches; (e) the slot has a length taken orthogonal to the long axis of 0.60, 0.61, 0.62, 0.63, 0.64, 0.66, 0.67, 0.68, 0.69, 0.70 inches; (f) the first protuberance extends orthogonal to the long axis and away from the first sidewall by 0.090, 0.091, 0.092, 0.093, 0.094, 0.096, 0.097, 0.098, 0.099, 0.100 inches, (g) or combinations thereof.

Figure 11:
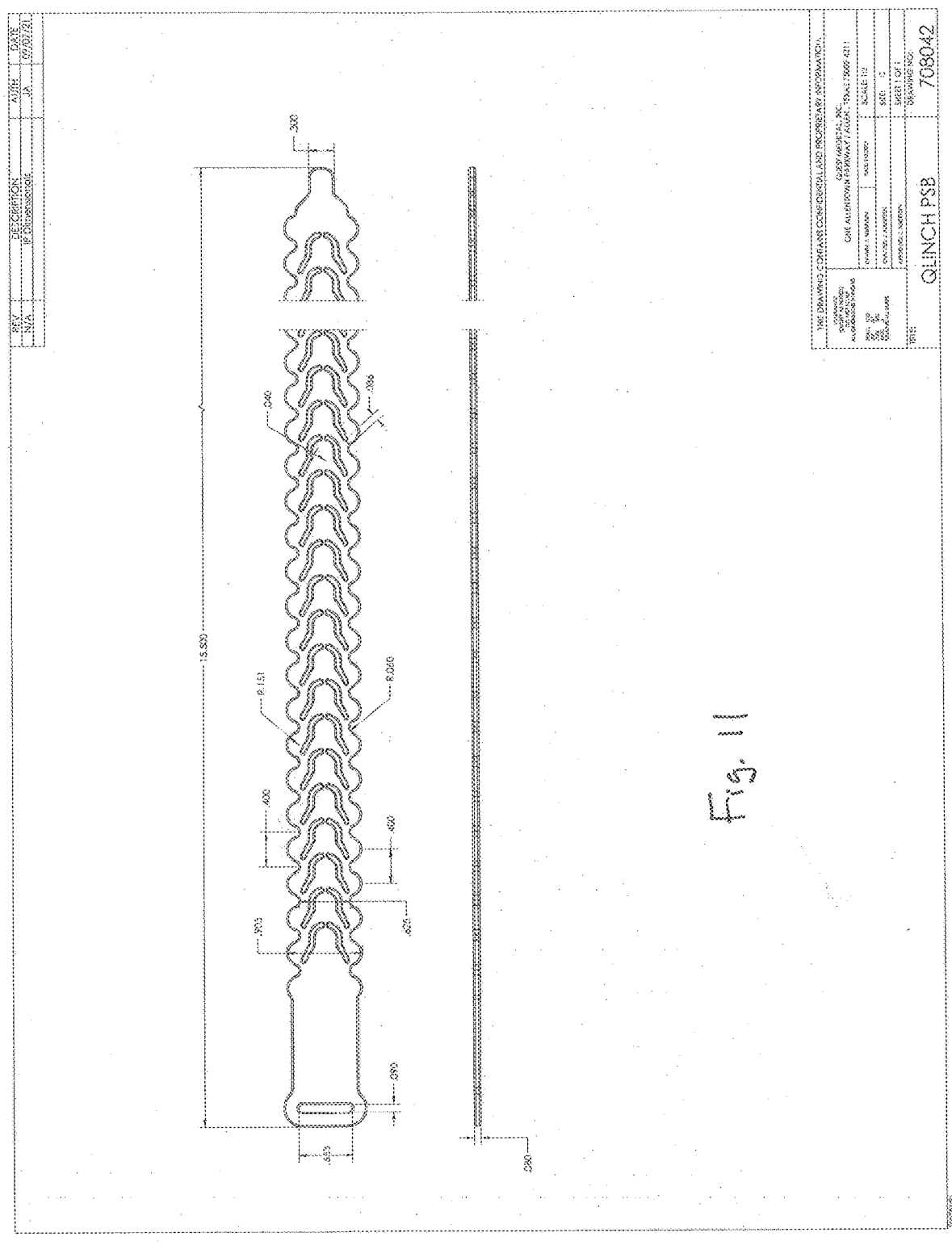
FIG. 11 shows example dimensions for an embodiment that includes a series of separable flaps, any of which may be separated from the IV band to adjust the length of the band to better fit around a portion of a patient, such as a patient's arm.
Figure 14:
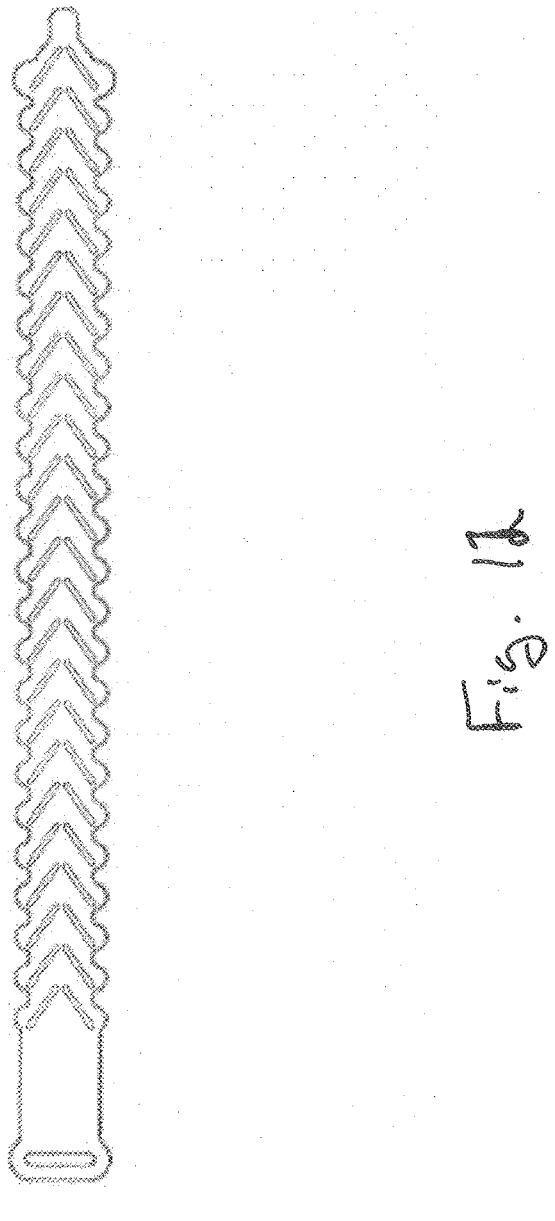

For example, in FIG. 11 the second width (0.905 inches) is wider than the first width (0.653 inches) by 0.252 inches. The second width is greater than the first width by a ratio of not greater than 1.4 (0.905/0.653=1.39). Regarding FIG. 11, other embodiments include dimensions where all dimensions increase by 1, 2, 3, 4, 5, 6, 7, 8, 9, 10% over the values shown in FIG. 11 or all dimensions decrease by 1, 2, 3, 4, 5, 6, 7, 8, 9, 10% over the values shown in FIG. 11.

Figure 4:
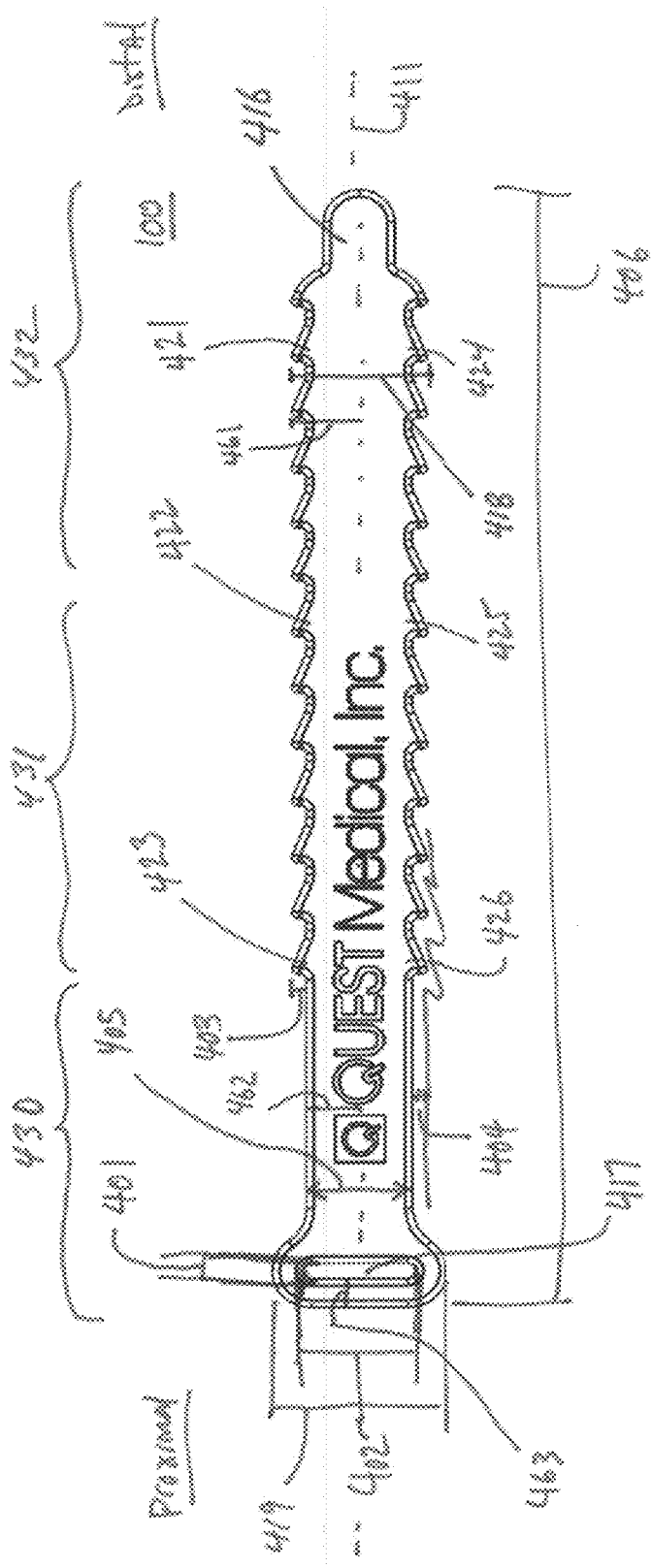
FIG. 4 includes an embodiment of a band.
Figure 5:
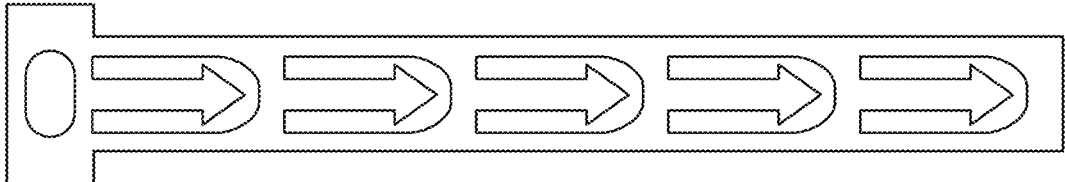
FIG. 5 includes an embodiment of a band.
Figure 8:
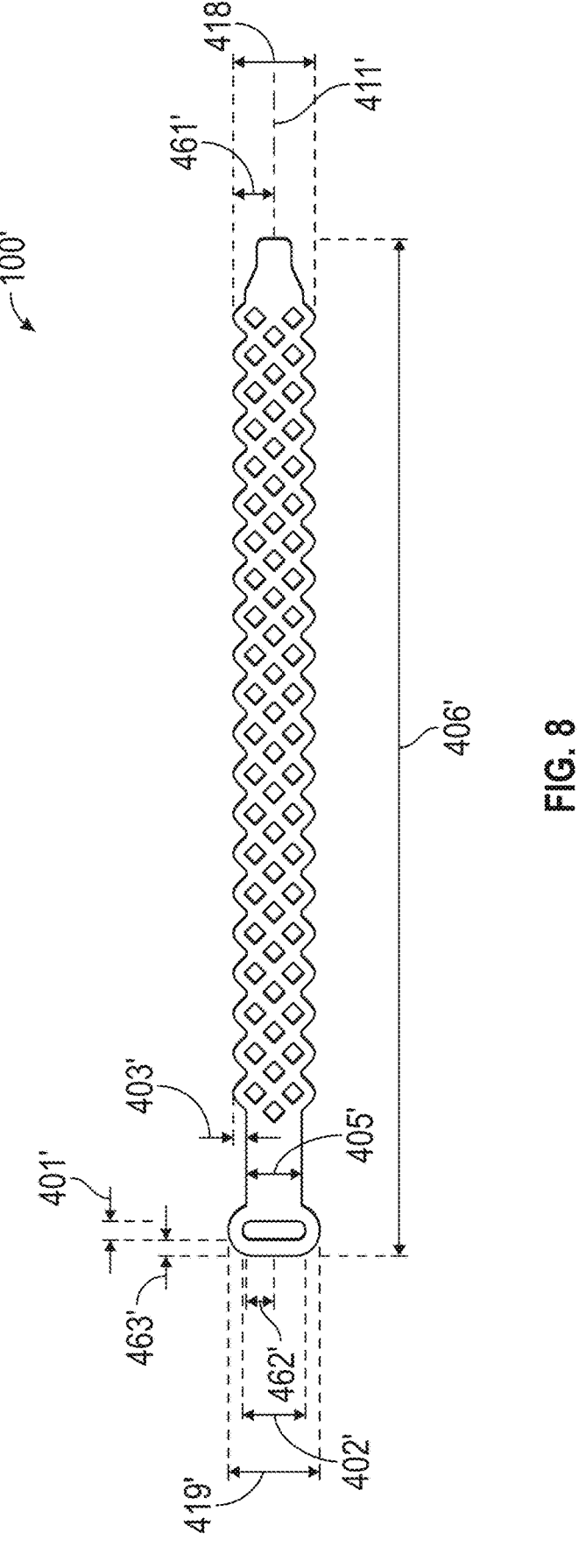
FIG. 8 includes an embodiment of a band.

These measurements are applicable to various embodiments, including those of FIGS. 4 and 8 (but are not limited thereto). The following dimensions may be critical in some embodiments (along with a material hardness between Shore A 30 and Shore A 50) to ensure the band "gives" when under a threshold level of expansive force (e.g., when securing an IV to a patient's arm): (a) the second width is wider than the first width by at least 0.08 inches but no more than 0.15 inches; (b) the third width is wider than the second width by at least 0.30 inches but no more than 0.40 inches.

Example 2. The band according to any of examples 1 or 13 comprising an additional band, the additional band comprising: an additional overall length defined along the long axis of the band; an additional proximal third, an additional distal third, and an additional middle third between the additional proximal and distal thirds; a substantially flat additional first face opposite a substantially flat additional second face. The additional band includes an additional first side wall opposite an additional second side wall, the additional first side wall coupling the additional first and second flat faces to each other and the additional second side wall also coupling the additional first and second flat faces to each other. The additional band includes a distal portion of the additional first sidewall, the distal portion of the additional first sidewall including additional first, second, and third protuberances, and a distal portion of the additional second sidewall, the distal portion of the additional second sidewall including additional fourth, fifth, and sixth protuberances. The additional band includes a proximal portion of the additional first sidewall, the proximal portion of the additional first sidewall including no protuberances, and a proximal portion of the additional second sidewall, the proximal portion of the additional second sidewall including no protuberances. The additional band includes a tip of the additional first protuberance that extends an additional first distance, orthogonal to the long axis, from the long axis; wherein the proximal portion of the additional first sidewall extends an additional second distance, orthogonal to the long axis, from the long axis and the additional first distance is greater than the additional second distance. The additional band includes an additional slot included in the proximal third of the additional band and including an additional first width that is orthogonal to the long axis. The additional band includes an additional second width extending orthogonal to the long axis and from the tip of the additional first protuberance to a tip of the additional fourth protuberance, wherein the additional second width is wider than the additional first width. The additional band includes an additional third width colinear with the additional first width and extending from the additional first side wall to the additional second sidewall, wherein the additional third width is wider than the additional second width. The additional band includes the resilient material. The additional first protuberance includes an additional leading edge that slopes away from the long axis as the additional leading edge extends proximally. The additional first protuberance includes an additional trailing edge that meets the additional first sidewall via an additional arcuate edge and slopes away from the long axis as the additional trailing edge extends distally. The additional leading edge is longer than the additional trailing edge. The additional leading edge has an additional first angle of incidence with the additional first sidewall, the additional trailing edge has an additional second angle of incidence with the additional first sidewall, and the additional first angle of incidence is less than the additional second angle of incidence. The additional band is monolithic with the band.

Figure 2:
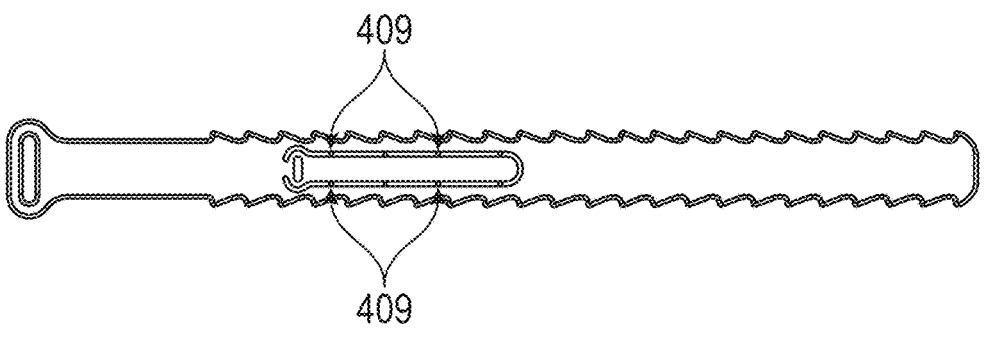
FIG. 2 includes an embodiment of a band that includes an additional band.
Figure 3:
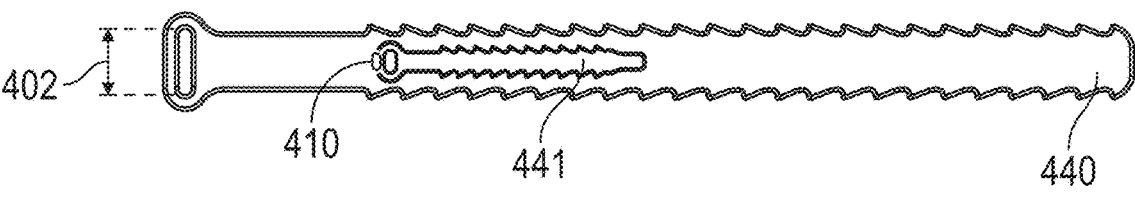
FIG. 3 includes an embodiment of a band that includes an additional band.

For example, see FIGS. 2, 3, 4.

Example 3. The band of example 2, wherein the third protuberance is proximal to the additional slot when the first face is substantially included in a plane.

Figures 6A, 6B, 6C:
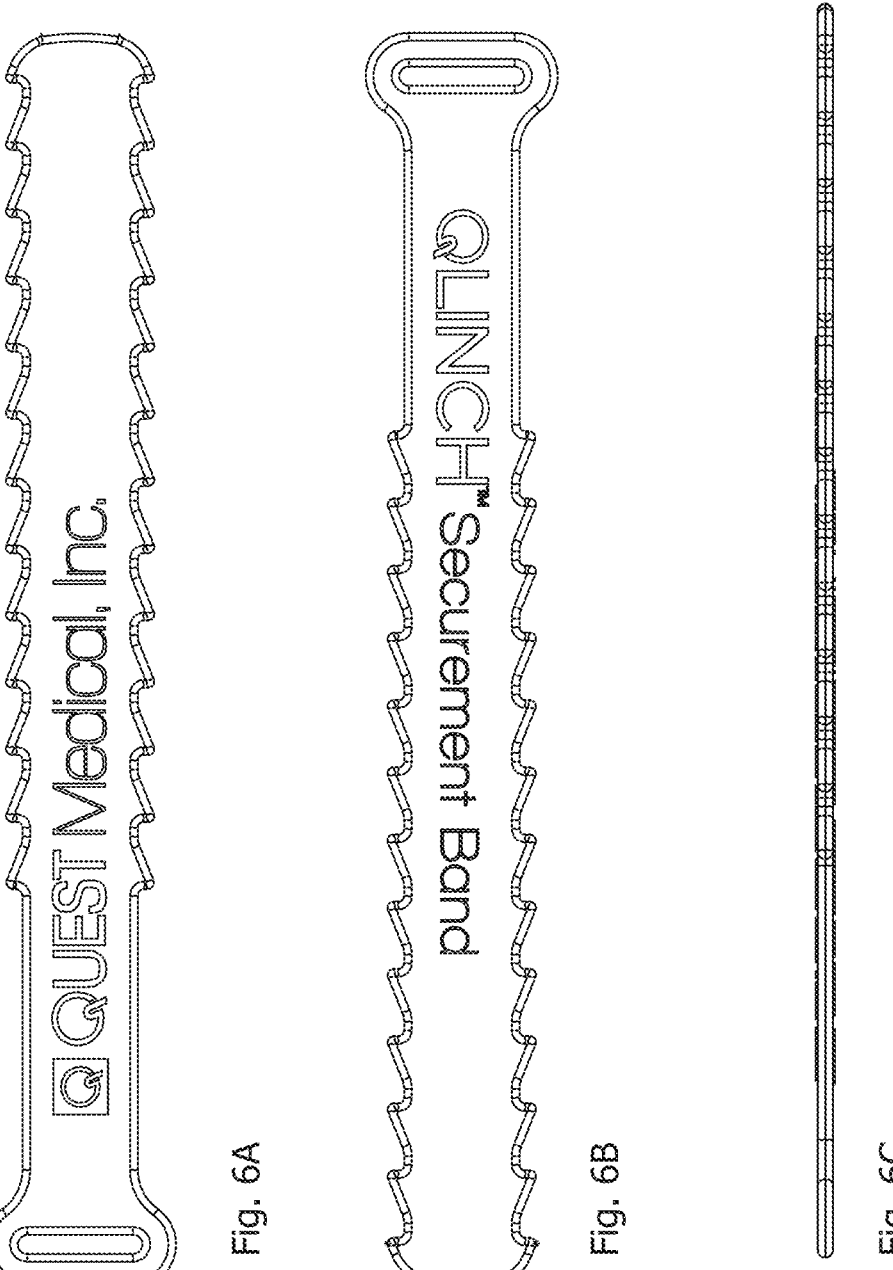
FIG. 6A includes a top view of an embodiment of a band.
FIG. 6B includes a bottom view of the embodiment of FIG. 6A.
FIG. 6C includes a side view of the embodiment of FIG. 6A.

For such an orientation (i.e., "when the first face is substantially included in a plane"), see FIG. 6C.

Example 4. A method comprising forming a loop by sliding the first protuberance of the band according to any of examples 1 or 13 through the slot to affix the band to an object located within the loop.

Figure 9:
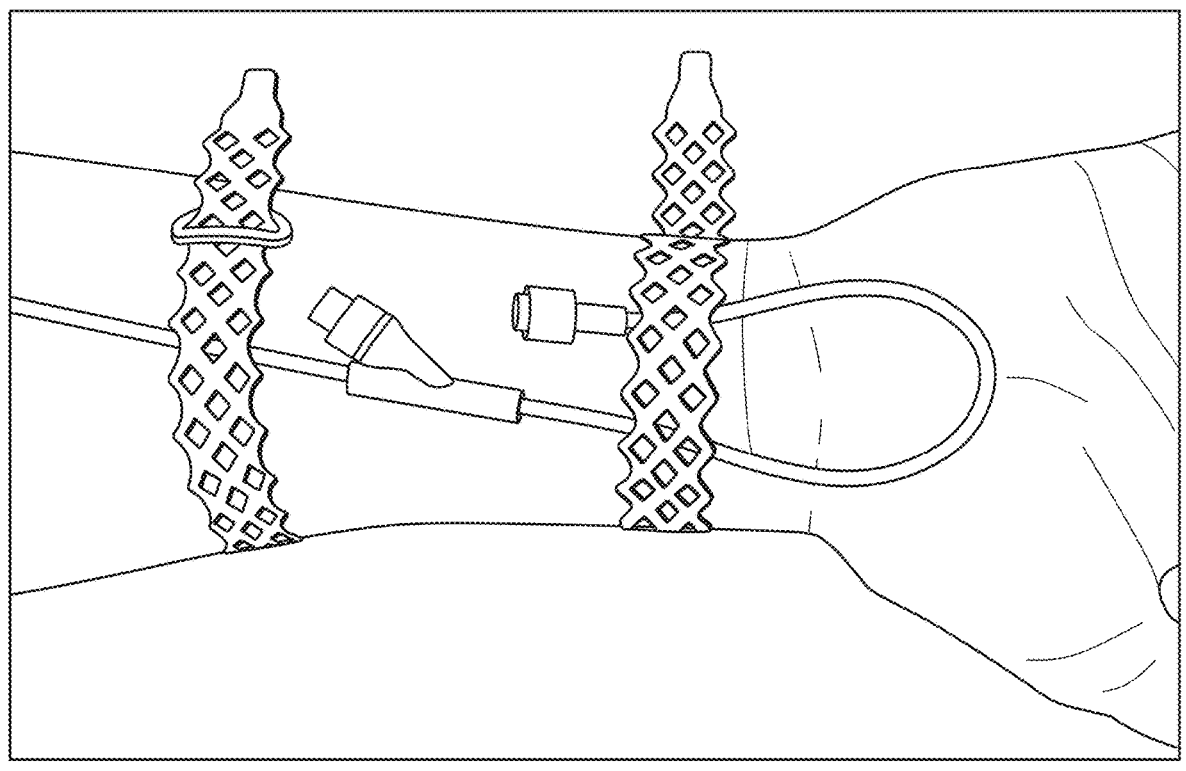
FIG. 9 includes embodiments of a band being used to secure an intravenous (IV) tube to a patient.

See, e.g., FIG. 9.

Example 5. The method of example 4 wherein the object includes a portion of a patient's body.

So, while some embodiments include a method for affixing a band to a non-human, other embodiments may include where the band acts as, for example, a bracelet (or larger bands could affix around a patient's thigh while smaller embodiments may affix around a patient's finger). The additional or sub-band may then be used to statically restrain an intravenous (IV) tube and the like. Collectively, the band and its sub-band may help secure a tube or conduit (e.g., IV tube) to a patient's appendage.

Example 6. The method of example 5 comprising forming an additional loop by sliding the additional first protuberance of the additional band of example 2 through the additional slot to affix the additional band to an additional object located within the additional loop Thus, a loop from the large band may encircle a patient's arm (or leg or waist) while a loop from the sub-band may encircle an IV tube, Foley catheter, and the like.

Example 7. The method of example 6 wherein the additional object includes at least one of an intravenous tube, a catheter, or combinations thereof.

Example 8. The band of example 3 wherein: the additional band couples to the band via a plurality of arms; the plurality of arms couples at least one of the distal or middle thirds of the additional band to at least one of the distal or middle thirds of the band.

For example, see arms 409.

Example 9. The band of example 8 wherein the plurality of arms is monolithic with the band and the additional band.

"Monolithic", as used herein, means formed or composed as a single piece of material without joints or seams, consisting of or constituting a single unit, constituting an undifferentiated whole. For example, the band may include a thermoplastic formed in a mold, extrusion molded, injection molding, and the like.

Example 10. The band of example 9 wherein: an additional arm couples the proximal third of the additional band to at least one of the proximal or middle thirds of the band; the additional arm has a greater surface area than each of the plurality of arms.

See, e.g., additional arm 410.

Example 11. The band to any of examples 1 or 13 wherein the resilient material includes at least one of a thermoplastic elastomer, silicone, rubber, or combinations thereof.

Example 12. The band of example 11 wherein the resilient material has a Shore A 40 hardness.

Example 12.1 The band of example 11 wherein the resilient material has a Shore A 30 hardness.

Example 12.2 The band of example 11 wherein the resilient material has a Shore A 50 hardness.

Example 13. A band comprising: an overall length defined along a long axis of the band; a proximal third, a distal third, and a middle third between the proximal and distal thirds. The band includes a substantially flat first face opposite a substantially flat second face. The band includes a first side wall opposite a second side wall, the first side wall coupling the first and second flat faces to each other and the second side wall also coupling the first and second flat faces to each other. The band includes a distal portion of the first sidewall, the distal portion of the first sidewall including first, second, and third protuberances, and a distal portion of the second sidewall, the distal portion of the second sidewall including fourth, fifth, and sixth protuberances. The band includes a proximal portion of the first sidewall, the proximal portion of the first sidewall including no protuberances, and a proximal portion of the second sidewall, the proximal portion of the second sidewall including no protuberances. The band includes a tip of the first protuberance that extends a first distance, orthogonal to the long axis, from the long axis. The proximal portion of the first sidewall extends a second distance, orthogonal the long axis, from the long axis and the first distance is greater than the second distance. The band includes a slot included in the proximal third of the band and including a first width that is orthogonal to the long axis. The band includes a second width extending orthogonal to the long axis and from the tip of the first protuberance to a tip of the fourth protuberance, wherein the second width is wider than the first width. The band includes a third width colinear with the first width and extending from the first side wall to the second sidewall, wherein the third width is wider than the second width. The band includes a resilient material. The first protuberance includes a leading edge that slopes away from the long axis as the leading edge extends proximally. The first protuberance includes a trailing edge that meets the first sidewall via an arcuate edge and slopes away from the long axis as the trailing edge extends distally. The leading edge is longer than the trailing edge. The leading edge has a first angle of incidence with the first sidewall, the trailing edge has a second angle of incidence with the first sidewall, and the first angle of incidence is less than the second angle of incidence. The slot has a width taken along the long axis. The slot has a length taken orthogonal to the long axis, the length of the slot being larger than the width of the slot. The band is monolithic and formed from a single structure with no fusions, welds, or adhesions between different sub-portions of the first band.

Thus, embodiments (such as embodiments in FIG. 10C or 11) are not limited to the dimensions addressed in example 1.

Another version of Example 13. A band comprising: an overall length defined along a long axis of the band; a proximal third, a distal third, and a middle third between the proximal and distal thirds. The band includes a substantially flat first face opposite a substantially flat second face. The band includes a first side wall opposite a second side wall, the first side wall coupling the first and second flat faces to each other and the second side wall also coupling the first and second flat faces to each other. The band includes a distal portion of the first sidewall, the distal portion of the first sidewall including first, second, and third protuberances, and a distal portion of the second sidewall, the distal portion of the second sidewall including fourth, fifth, and sixth protuberances. The band includes a proximal portion of the first sidewall, the proximal portion of the first sidewall including no protuberances, and a proximal portion of the second sidewall, the proximal portion of the second sidewall including no protuberances. The band includes a tip of the first protuberance that extends a first distance, orthogonal to the long axis, from the long axis. The proximal portion of the first sidewall extends a second distance, orthogonal the long axis, from the long axis and the first distance is greater than the second distance. The band includes a slot included in the proximal third of the band and including a first width that is orthogonal to the long axis. The band includes a second width extending orthogonal to the long axis and from the tip of the first protuberance to a tip of the fourth protuberance, wherein the second width is wider than the first width. The band includes a third width colinear with the first width and extending from the first side wall to the second sidewall, wherein the third width is wider than the second width. The band includes a resilient material. The first protuberance includes a leading edge that slopes away from the long axis as the leading edge extends proximally. The first protuberance includes a trailing edge. The slot has a width taken along the long axis. The band is monolithic and formed from a single structure with no fusions, welds, or adhesions between different sub-portions of the first band.

For instance, see FIG. 8.

Example 14. The band of example 13 wherein the second width the second width is wider than the first width by a range of 0.10 to 0.15 inches.

Example 15. The band according to at least one of example 1 or 13 wherein there is no negative space between any portion of the trailing edge and the tip of the first protuberance.

Figure 7:
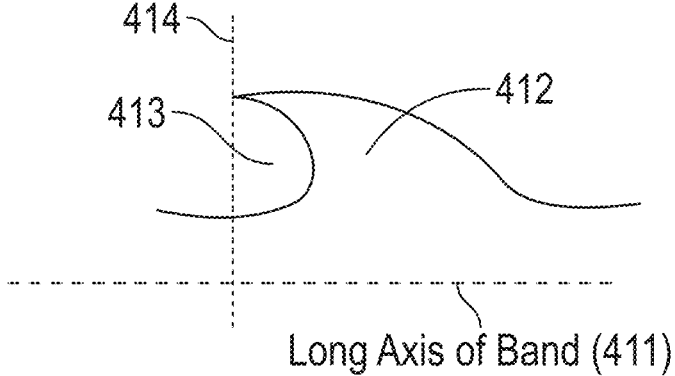
FIG. 7 includes an embodiment of a band's protuberance.

For example, FIG. 7 shows a long axis 411 of the band orthogonal to axis 414. Protuberance 412 has a "negative space" 413, whereas no such negative space exists in the embodiment of FIG. 4. As a result, the embodiment of FIG. 4 may more easily loosen to prevent tube occlusion once a threshold band expansion force is met and may be more easily removed from molds during manufacturing. However, some embodiments may include such negative spaces.

Example 16. The band of example 15, wherein an axis, which is orthogonal to the long axis, intersects the first sidewall and the tip of the first protuberance without traversing a void between the first sidewall and the tip of the first protuberance.

For example, see axis 415 (FIG. 1A) as compared to axis 414 (FIG. 7).

Example 17. The band according to at least one of examples 1 or 13, wherein tightening the band by simultaneously advancing one of the first, second, and third protuberances and one of the fourth, fifth, and sixth protuberances through the slot requires between 1 and 4 pounds of force.

For example, such force measurements may be obtained by affixing an FDX Force Ten (model FDX 50) (by Wagner Instruments) to distal tip 416. Tip 416 may be advanced through slot 417 and then tip 416 is attached to the force gauge. The gauge is then used to pull the tip and thereby tighten the band loop and incrementally advance teeth in pairs through the slot. For example, see first (421), second (422), and third (423) protuberances and one of the fourth (424), fifth (425), and sixth (426) protuberances with pairs (421, 424), (422, 425), (423, 426). While in this example there are other protuberances between the first, second, and third protuberances in other embodiments the protuberances may be consecutive such that no protuberances are between the first and second protuberances or between the second and third protuberances. Further, the first, second, and third protuberances may be located in proximal (430), middle (431), or distal (432) portions of the band.

Example 17.1 The band of example 17, wherein: tightening the band by simultaneously advancing the third and sixths protuberance through the slot takes more force than tightening the band by simultaneously advancing the first and fourth protuberances through the slot. The third protuberance is proximal to the first protuberance when the first face is substantially included in a plane. The sixth protuberance is proximal to the fourth protuberance when the first face is substantially included in the plane.

For example, for a series of consecutive teeth the force grew (from a distal tooth with a larger loop to a more proximal tooth with a smaller loop) as follows (in pounds of force): 1.1, 1.2, 1.2, 1.7, 2.15, 2.25, 3.6, 5.0. The progression may have some aberration but generally increases.

Example 18. The band according to at least one of examples 1, 13, or 17, wherein loosening the band by simultaneously withdrawing one of the first, second, and third protuberances and one of the fourth, fifth, and sixth protuberances through the slot requires between 1 and 4.0 pounds of force.

For example, such force measurements may be obtained by affixing an FDX Force Ten (model FDX 50) an inch or so proximal of the slot "within the loop" (whereas during tightening the gauge was attached to the band distal tip). The gauge is then used to pull the band and thereby loosen the band loop and incrementally withdraw teeth in pairs through the slot.

Example 18.1 The band of example 18, wherein: loosening the band by simultaneously withdrawing the third and sixths protuberances through the slots takes more force than loosening the band by simultaneously withdrawing the first and fourth protuberances through the slot. The third protuberance is proximal to the first protuberance when the first face is substantially included in a plane. The sixth protuberance is proximal to the fourth protuberance when the first face is substantially included in the plane.

For example, for a series of consecutive teeth the force grew (from a proximal tooth with a smaller loop to a more distal tooth with a larger loop) as follows (in pounds of force): 3.75, 3.9, 3.25, 2.35, 1.3, 1.15, 1.1. Thus, the progression may have some aberration but generally decreases.

Example 19. The band of example 13, wherein the second width is greater than the first width by a ratio not greater than 1.4.

Another version of Example 19. The band of example 13, wherein the second width is greater than the first width by a ratio no greater than 1.4.

Example 19.1 The band of example 2 wherein the additional second width is greater than the additional first width by a ratio not greater than 1.4.

Thus, in FIG. 3 the second band 441 may have the same ratios as band 440. These ratios may exist for other values such as, for example, length to width (406:405), tooth length to width (407:405), tooth length to sidewall width along the slot (407:408), and the like.

Example 20. The band of example 19, wherein the ratio is between 1.1 and 1.2.

Example 21. A band comprising: an overall length defined along a long axis of the band. The band includes a proximal third, a distal third, and a middle third between the proximal and distal thirds. The band includes a substantially flat first face opposite a substantially flat second face. The band includes a first side wall opposite a second side wall, the first side wall coupling the first and second flat faces to each other and the second side wall also coupling the first and second flat faces to each other. The band includes a distal portion of the first sidewall, the distal portion of the first sidewall including first, second, and third protuberances, and a distal portion of the second sidewall, the distal portion of the second sidewall including fourth, fifth, and sixth protuberances. The band includes a proximal portion of the first sidewall, the proximal portion of the first sidewall including no protuberances, and a proximal portion of the second sidewall, the proximal portion of the second sidewall including no protuberances. The band includes a tip of the first protuberance that extends a first distance, orthogonal to the long axis, from the long axis, wherein the proximal portion of the first sidewall extends a second distance, orthogonal the long axis, from the long axis and the first distance is greater than the second distance. The band includes a slot included in the proximal third of the band and including a first width that is orthogonal to the long axis. The band includes a second width extending orthogonal to the long axis and from the tip of the first protuberance to a tip of the fourth protuberance, wherein the second width is greater than the first width by a ratio no greater than 1.4. The band includes a resilient material, wherein the resilient material has one of a Shore A 30 hardness, Shore A 40 hardness, or a Shore A 50 hardness. The first protuberance includes a leading edge that slopes away from the long axis as the leading edge extends proximally. The first protuberance includes a trailing edge that meets the first sidewall via an arcuate edge and slopes away from the long axis as the trailing edge extends distally. The leading edge is longer than the trailing edge. The leading edge has a first angle of incidence with the first sidewall, the trailing edge has a second angle of incidence with the first sidewall, and the first angle of incidence is less than the second angle of incidence.

Example 22. A band comprising: a substantially flat first face opposite a substantially flat second face. The band includes a first side wall opposite a second side wall, the first and second side walls coupling the first and second flat faces to each other. The band includes a distal portion of the first sidewall including first, second, and third protuberances, and a distal portion of the second sidewall including fourth, fifth, and sixth protuberances. The band includes a slot including a first width. The band includes a second width, extending from the tip of the first protuberance to a tip of the fourth protuberance, which is greater than the first width by a ratio no greater than 1.4. The band includes a resilient material that has one of a Shore A 30 hardness, Shore A 40 hardness, or a Shore A 50 hardness. The first protuberance includes a leading edge that slopes away from a long axis of the band as the leading edge extends proximally. The first protuberance includes a trailing edge that meets the first sidewall via an arcuate edge and slopes away from the long axis as the trailing edge extends distally. The leading edge is longer than the trailing edge. The leading edge has a first angle of incidence with the first sidewall, the trailing edge has a second angle of incidence with the first sidewall, and the first angle of incidence is less than the second angle of incidence.

Example 23. A band comprising: a first face opposite a second face. The band includes a first side wall opposite a second side wall, the first and second side walls coupling the first and second faces to each other. The band includes a distal portion of the first sidewall including first, second, and third protuberances, and a distal portion of the second sidewall including fourth, fifth, and sixth protuberances. The band includes an aperture including a first width; a second width, extending from the tip of the first protuberance to a tip of the fourth protuberance, which is greater than the first width by a ratio no greater than 1.4. The band includes a resilient material that has one of a Shore A 30 hardness, Shore A 40 hardness, or a Shore A 50 hardness. The first protuberance includes a leading edge that slopes away from a long axis of the band as the leading edge extends proximally. The first protuberance includes a trailing edge that meets the first sidewall via an arcuate edge and slopes away from the long axis as the trailing edge extends distally. The leading edge is longer than the trailing edge. The leading edge has a first angle of incidence with the first sidewall, the trailing edge has a second angle of incidence with the first sidewall, and the first angle of incidence is less than the second angle of incidence.

Thus, faces of the band do not necessarily have to be wholly or partially flat. However, in some embodiments (FIG. 6C) the faces are entirely flat. Still, other embodiments may have a circular or ovular cross-section with teeth along one (yes, embodiments include those where teeth are not in pairs but only a single row or series of teeth on a single side of a band exist) or two edges or teeth that circumscribe the body of the band. The slot may be circular, ovular, and the like. Sidewalls may be portions of a circular or ovular wall that generally are on a "side" rather than "top" or "bottom" of a band.

Example 24. A band comprising: a first face opposite a second face. The band includes a first side wall opposite a second side wall, the first and second side walls coupling the first and second faces to each other. The band includes a distal portion of the first sidewall including first, second, and third protuberances, and a distal portion of the second sidewall including fourth, fifth, and sixth protuberances. The band includes an aperture including a first width. The band includes a second width, extending from the tip of the first protuberance to a tip of the fourth protuberance, which is greater than the first width. The band includes a resilient material. The first protuberance includes a leading edge that slopes away from a long axis of the band as the leading edge extends proximally. The first protuberance includes a trailing edge that meets the first sidewall via an arcuate edge and slopes away from the long axis as the trailing edge extends distally. The leading edge is longer than the trailing edge. The leading edge has a first angle of incidence with the first sidewall, the trailing edge has a second angle of incidence with the first sidewall, and the first angle of incidence is less than the second angle of incidence. The first width, the second width, and a hardness of the resilient material are configured such that the band automatically loosens by withdrawing the third and sixths protuberance through the slot when expansive forces on the band are between and 1 and 5 pounds.

Example 25. A band comprising: a first face opposite a second face. The band includes a first side wall opposite a second side wall, the first and second side walls coupling the first and second faces to each other. The band includes a distal portion of the first sidewall including first, second, and third protuberances, and a distal portion of the second sidewall including fourth, fifth, and sixth protuberances. The band includes an aperture including a first width. The band includes a second width, extending from the tip of the first protuberance to a tip of the fourth protuberance, which is greater than the first width. The band includes a resilient material. The first protuberance includes a leading edge that slopes away from a long axis of the band as the leading edge extends proximally. The first protuberance includes a trailing edge that meets the first sidewall via an arcuate edge and slopes away from the long axis as the trailing edge extends distally. The leading edge is longer than the trailing edge. The leading edge has a first angle of incidence with the first sidewall, the trailing edge has a second angle of incidence with the first sidewall, and the first angle of incidence is less than the second angle of incidence. The band includes a means for automatically loosening the band by withdrawing the third and sixth protuberances through the slot when expansive forces on the band are between and 1 and 5 pounds.

Example 26. A band comprising: a first face opposite a second face. The band includes a first side wall opposite a second side wall, the first and second side walls coupling the first and second faces to each other. The band includes a distal portion of the first sidewall including first, second, and third protuberances, and a distal portion of the second sidewall including fourth, fifth, and sixth protuberances. The band includes an aperture including a first width. The band includes a second width, extending from the tip of the first protuberance to a tip of the fourth protuberance, which is greater than the first width by a ratio no greater than 1.4. The band includes a resilient material that has one of a Shore A 30 hardness, Shore A 40 hardness, or a Shore A 50 hardness. The first protuberance includes a shark fin shape.

Example 27. A band comprising: an overall length defined along a long axis of the band. The band includes a proximal third, a distal third, and a middle third between the proximal and distal thirds. The band includes a first face opposite a second face. The band includes a first side wall opposite a second side wall, the first side wall coupling the first and second faces to each other and the second side wall also coupling the first and second faces to each other. The band includes a distal portion of the first sidewall, the distal portion of the first sidewall including first, second, and third protuberances, and a distal portion of the second sidewall, the distal portion of the second sidewall including fourth, fifth, and sixth protuberances. The band includes a proximal portion of the first sidewall, the proximal portion of the first sidewall including no protuberances, and a proximal portion of the second sidewall, the proximal portion of the second sidewall including no protuberances. The band includes a tip of the first protuberance that extends a first distance, orthogonal to the long axis, from the long axis, wherein the proximal portion of the first sidewall extends a second distance, orthogonal the long axis, from the long axis and the first distance is greater than the second distance. The band includes a slot included in the proximal third of the band and including a first width that is orthogonal to the long axis. The band includes a second width extending orthogonal to the long axis and from the tip of the first protuberance to a tip of the fourth protuberance, wherein the second width is greater than the first width by a ratio no greater than 1.4. The band includes a resilient material, wherein the resilient material has one of a Shore A 30 hardness, Shore A 40 hardness, or a Shore A 50 hardness. The first protuberance includes a leading edge that slopes away from the long axis as the leading edge extends proximally. The first protuberance includes a trailing edge; (c) the leading edge is longer than the trailing edge. The leading edge has a first angle of incidence with the first sidewall, the trailing edge has a second angle of incidence with the first sidewall, and the first angle of incidence is less than the second angle of incidence.

Thus, in an embodiment the trailing edge does not necessarily have a non-orthogonal angle of incidence or interface a band sidewall with an arcuate edge.

Example 28. A system comprising a band and metal structure. The band includes an overall length defined along a long axis of the band. The band includes a proximal third, a distal third, and a middle third between the proximal and distal thirds. The band includes a first face opposite a second face. The band includes a first side wall opposite a second side wall, the first side wall coupling the first and second faces to each other and the second side wall also coupling the first and second faces to each other. The band includes a distal portion of the first sidewall, the distal portion of the first sidewall including first, second, and third protuberances, and a distal portion of the second sidewall, the distal portion of the second sidewall including fourth, fifth, and sixth protuberances. The band includes a proximal portion of the first sidewall, the proximal portion of the first sidewall including no protuberances, and a proximal portion of the second sidewall, the proximal portion of the second sidewall including no protuberances. The band includes a tip of the first protuberance that extends a first distance, orthogonal to the long axis, from the long axis, wherein the proximal portion of the first sidewall extends a second distance, orthogonal the long axis, from the long axis and the first distance is greater than the second distance. The band includes a slot included in the proximal third of the band and including a first width that is orthogonal to the long axis. The band includes a second width extending orthogonal to the long axis and from the tip of the first protuberance to a tip of the fourth protuberance, wherein the second width is greater than the first width by a ratio no greater than 1.4. The band includes a resilient material, wherein the resilient material has one of a Shore A 30 hardness, Shore A 40 hardness, or a Shore A 50 hardness. The first protuberance includes a leading edge that slopes away from the long axis as the leading edge extends proximally. The first protuberance includes a trailing edge. The leading edge is longer than the trailing edge. The leading edge has a first angle of incidence with the first sidewall, the trailing edge has a second angle of incidence with the first sidewall, and the first angle of incidence is less than the second angle of incidence. The band is formed in a loop around the metal structure.

Example 29. A kit including a plurality of any of the bands according to any of examples 1-23, wherein the at least two of the bands are colored different from one another.

For example, a colorX may be used by a nursing staff for functionX (afferent tubing carrying fluid to patient) while colorY is used by the staff for function (efferent tubing carrying tubing away from patient). Instead of or in addition to changing colors, lengths of bands in the kit may vary as well.

Example 30. A band comprising a substantially flat first face opposite a substantially flat second face. The band includes a first side wall opposite a second side wall, the first and second side walls coupling the first and second flat faces to each other. The band includes a distal portion of the first sidewall including first, second, and third protuberances, and a distal portion of the second sidewall including fourth, fifth, and sixth protuberances. The band includes a slot including a first width that is orthogonal to a long axis of the band. The band includes a second width, extending from the tip of the first protuberance to the second sidewall, which is greater than the first width by a ratio no greater than 1.4. The band includes a resilient material that has hardness not softer than a Shore A 30 hardness and not hard than a Shore A 50 hardness. The first protuberance includes a leading edge that slopes away from a long axis of the band as the leading edge extends proximally and the first protuberance includes a trailing edge. The band is monolithic and formed from a single structure with no fusions, welds, or adhesions between different sub-portions of the first band.

For instance, see FIGS. 4 and/or 8.

FIG. 8 includes dimensions for a band 100' with a hole having width 401', length 402', teeth that protrude from the body by distance 403', width of body without teeth having width 405', length 406'. The proximal third extends along the long axis and is proximal to the slot by distance 463'. The slot has a width 401' taken along the long (long) axis. The slot has a length 402' (sometimes referred to as a width) taken orthogonal to the long axis. The band is monolithic and formed from a single structure with no fusions, welds, or adhesions between different sub-portions of the first band. First distance 461' is greater than second distance 462' with regard to axis 411'.

When Example 30 provides: "The band includes a second width, extending from the tip of the first protuberance to the second sidewall, which is greater than the first width by a ratio greater than 1.4." Such a second width may include distance 418'. For instance, the second width may extend between two opposing protuberances. However, the distance may also extend, orthogonal to the long axis, from one protuberance to a portion of an opposing sidewall that has no protuberance.

Example 31. The band of example 30 comprising an overall length defined along the long axis. The band includes at least 5 apertures located between the slot and a distal tip of the band, the slot being located adjacent a proximal tip of band. The at least 5 apertures extend along a majority of the overall length.

For instance, see FIG. 8. By changing the angle of incidence for the trailing edge of a protuberance from 90 degrees (e.g., FIG. 4) to 135 degrees (e.g., FIG. 8), the embodiment will "self-adjust" more freely to prevent over-tightening and prevent constricting a patient's blood vessels (e.g., when being used to secure an IV to a patient's arm such as in FIG. 9). Additionally, the "lattice structure" helps the band shrink/compress along the long axis of the band to assist with the "self-adjustment" and prevent over-tightening. Thus, some embodiments may have an angle of instance for the trailing edge of 90 degrees while others may be 135 degrees or some measure in between 150 and 90 degrees.

Example 1a. An intravenous (IV) securement band comprising: (1) an overall length defined along a long axis of the band; (2) a proximal third, a distal third, and a middle third between the proximal and distal thirds; (3) a substantially flat first face opposite a substantially flat second face; (4) a first side wall opposite a second side wall, the first side wall coupling the first and second flat faces to each other and the second side wall also coupling the first and second flat faces to each other; (5) a distal portion of the first sidewall, the distal portion of the first sidewall including first, second, and third protuberances, and a distal portion of the second sidewall, the distal portion of the second sidewall including fourth, fifth, and sixth protuberances; (6) a proximal portion of the first sidewall, the proximal portion of the first sidewall including no protuberances, and a proximal portion of the second sidewall, the proximal portion of the second sidewall including no protuberances; (7) a tip of the first protuberance that extends a first distance, orthogonal to the long axis, from the long axis. The proximal portion of the first sidewall extends a second distance, orthogonal the long axis, from the long axis and the first distance is greater than the second distance. A slot is included in the proximal third of the band and including a first width that is orthogonal to the long axis. A second width extends orthogonal to the long axis and from the tip of the first protuberance to a tip of the fourth protuberance, wherein the second width is wider than the first width. A third width is colinear with the first width and extends from the first side wall to the second sidewall, wherein the third width is wider than the second width. The band includes a resilient material and a first flap (1070) having proximal portions (1071, 1072), the proximal portions of the first flap tapering outwardly away from the long axis (1011) and towards the first and second sidewalls as the proximal portions of the first flap extend proximally towards the slot. The band includes a second flap (1073) having proximal portions (1074, 1075), the proximal portions of the second flap tapering outwardly away from the long axis and towards the first and second sidewalls as the proximal portions of the second flap extend proximally towards the slot, the second flap being proximal to the first flap. The band includes first and second voids (1076, 1077) that are not contiguous with one another and which do not connect to either of the first or second sidewalls. A first axis (1078), which is orthogonal to the long axis, intersects the first and second sidewalls, the proximal portions of the first flap, and the first and second voids. The band is monolithic and formed from a single structure with no fusions, welds, or adhesions between different sub-portions of the first band.

Another version of Example 1a. An intravenous (IV) securement band comprising: an overall length defined along a long axis of the band; a proximal third, a distal third, and a middle third between the proximal and distal thirds; a substantially flat first face opposite a substantially flat second face; a first side wall opposite a second side wall, the first side wall coupling the first and second flat faces to each other and the second side wall also coupling the first and second flat faces to each other; a distal portion of the first sidewall, the distal portion of the first sidewall including first, second, and third protuberances, and a distal portion of the second sidewall, the distal portion of the second sidewall including fourth, fifth, and sixth protuberances; a slot included in the proximal third of the band and including a first width that is orthogonal to the long axis; a second width extending orthogonal to the long axis and from the tip of the first protuberance to a tip of the fourth protuberance, wherein the second width is wider than the first width; a resilient material; a first flap (1070) having proximal portions (1071, 1072), the proximal portions of the first flap tapering outwardly away from the long axis (1011) and towards the first and second sidewalls as the proximal portions of the first flap extend proximally towards the slot; a second flap (1073) having proximal portions (1074, 1075), the proximal portions of the second flap tapering outwardly away from the long axis and towards the first and second sidewalls as the proximal portions of the second flap extend proximally towards the slot, the second flap being proximal to the first flap; first and second voids (1076, 1077) that are not contiguous with one another and which do not connect to either of the first or second sidewalls; wherein a first axis (1078), which is orthogonal to the long axis, intersects the first and second sidewalls, the proximal portions of the first flap, and the first and second voids; wherein the band is monolithic and formed from a single structure with no fusions, welds, or adhesions between different sub-portions of the first band.

Another version of Example 1a: An intravenous (IV) securement band comprising: an overall length defined along a long axis of the band; a proximal third, a distal third, and a middle third between the proximal and distal thirds; a substantially flat first face opposite a substantially flat second face; a first side wall opposite a second side wall, the first side wall coupling the first and second flat faces to each other and the second side wall also coupling the first and second flat faces to each other; a distal portion of the first sidewall, the distal portion of the first sidewall including first, second, and third protuberances, and a distal portion of the second sidewall, the distal portion of the second sidewall including fourth, fifth, and sixth protuberances; a proximal portion of the first sidewall, the proximal portion of the first sidewall including no protuberances, and a proximal portion of the second sidewall, the proximal portion of the second sidewall including no protuberances; a tip of the first protuberance that extends a first distance, orthogonal to the long axis, from the long axis; wherein the proximal portion of the first sidewall extends a second distance, orthogonal the long axis, from the long axis and the first distance is greater than the second distance; a slot included in the proximal third of the band and including a first width that is orthogonal to the long axis; a second width extending orthogonal to the long axis and from the tip of the first protuberance to a tip of the fourth protuberance, wherein the second width is wider than the first width; a third width colinear with the first width and extending from the first side wall to the second sidewall, wherein the third width is wider than the second width; a resilient material; a first flap (1070) having proximal portions (1071, 1072), the proximal portions of the first flap tapering outwardly away from the long axis (1011) and towards the first and second sidewalls as the proximal portions of the first flap extend proximally towards the slot; a second flap (1073) having proximal portions (1074, 1075), the proximal portions of the second flap tapering outwardly away from the long axis and towards the first and second sidewalls as the proximal portions of the second flap extend proximally towards the slot, the second flap being proximal to the first flap; first and second voids (1076, 1077) that are not contiguous with one another and which do not connect to either of the first or second sidewalls; a means for automatically loosening the IV securement band by withdrawing the third and sixth protuberances through the slot when expansive forces on the band are between and 1 and 5 pounds; wherein a first axis (1078), which is orthogonal to the long axis, intersects the first and second sidewalls, the proximal portions of the first flap, and the first and second voids; wherein the band is monolithic and formed from a single structure with no fusions, welds, or adhesions between different sub-portions of the first band.

In an embodiment the "means for automatically loosening the IV securement band" includes: (a) the second width being greater than the first width by a ratio not greater than 1.4; (b) the resilient material having a hardness not softer than a Shore A 30 hardness and not harder than a Shore A 50 hardness.

In an embodiment the "means for automatically loosening the IV securement band" includes: (a) the second width being greater than the first width by a ratio not lower than 1.1 and not greater than 1.5; (b) the resilient material having a hardness not softer than a Shore A 30 hardness and not harder than a Shore A 50 hardness.

In an embodiment the "means for automatically loosening the IV securement band" includes: (a) the second width being greater than the first width by a ratio not greater than 1.5; (b) the resilient material having a hardness not softer than a Shore A 30 hardness and not harder than a Shore A 50 hardness.

In an embodiment the "means for automatically loosening the IV securement band" includes: (a) the second width being greater than the first width by a ratio not greater than 1.4; (b) the resilient material having a hardness not softer than a Shore A 30 hardness and not harder than a Shore A 50 hardness.

Example 2a. The IV securement band of Example 1a comprising third and fourth voids (1079, 1080) that are not contiguous with one another and which do not connect to either of the first or second sidewalls; wherein a second axis (1081), which is orthogonal to the long axis, intersects the first and second sidewalls, the proximal portions of the second flap, and the third and fourth voids.

Example 3a. The IV securement band of Example 2a, wherein the first axis intersects the third and fourth voids.

For example, there may be some overlap (radially) between voids such as the first and third voids.

Example 4a. The IV securement band according to any of Examples 1a-3a, wherein: the first and second voids are separated from each other by a solid portion (1082) of the band; the long axis intersects the solid portion of the band.

Example 5a. The IV securement band according to any of Examples 1a-4a, wherein: the first void is separated from the first sidewall by a first solid portion (1083) of the band; the second void is separated from the second sidewall by a second solid portion (1084) of the band; the first axis intersects the first and second solid portions of the band.

Figure 10A:
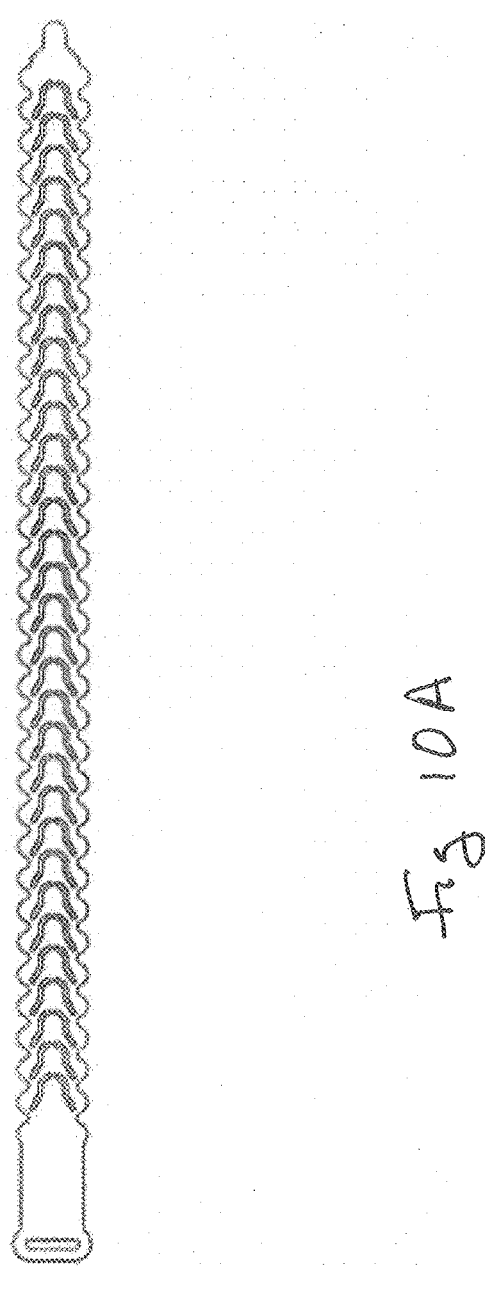
FIG. 10A shows an embodiment including a series of separable flaps, any of which may be separated from the IV band to adjust the length of the IV band.
Figure 10B:
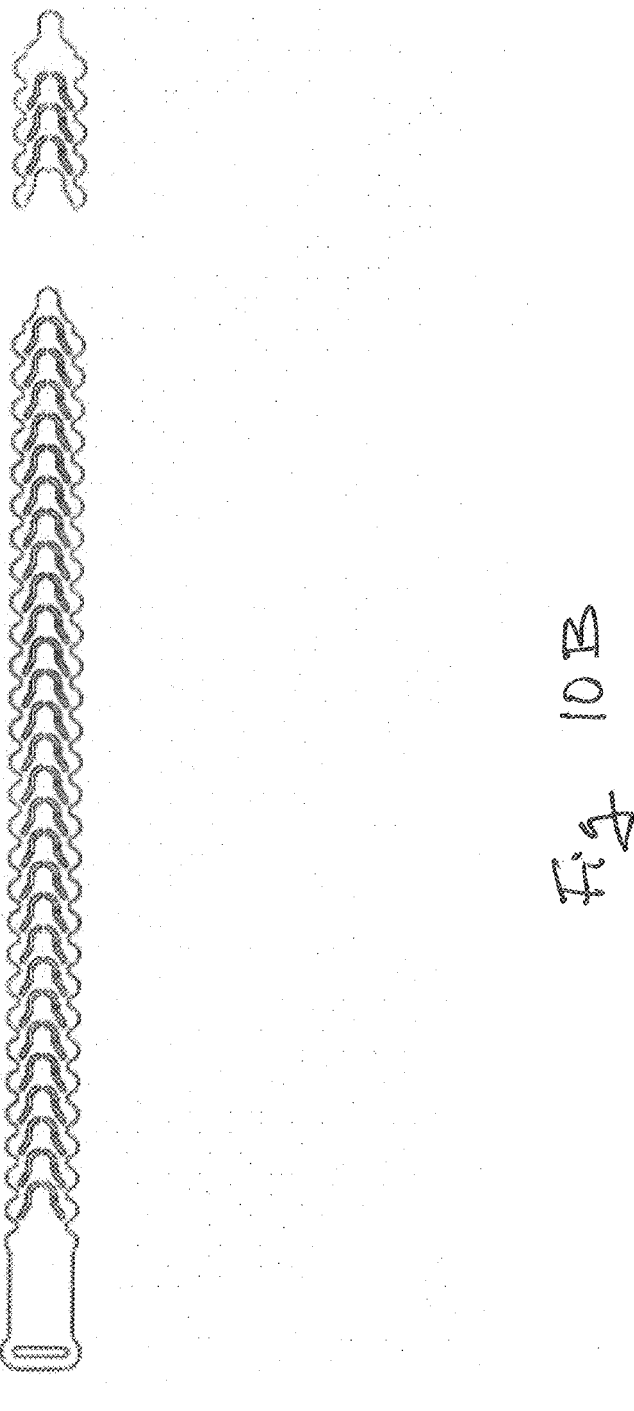
FIG. 10B shows an instance where a distal portion of the IV band has been separated from a proximal portion of the IV band.
Figure 10C:
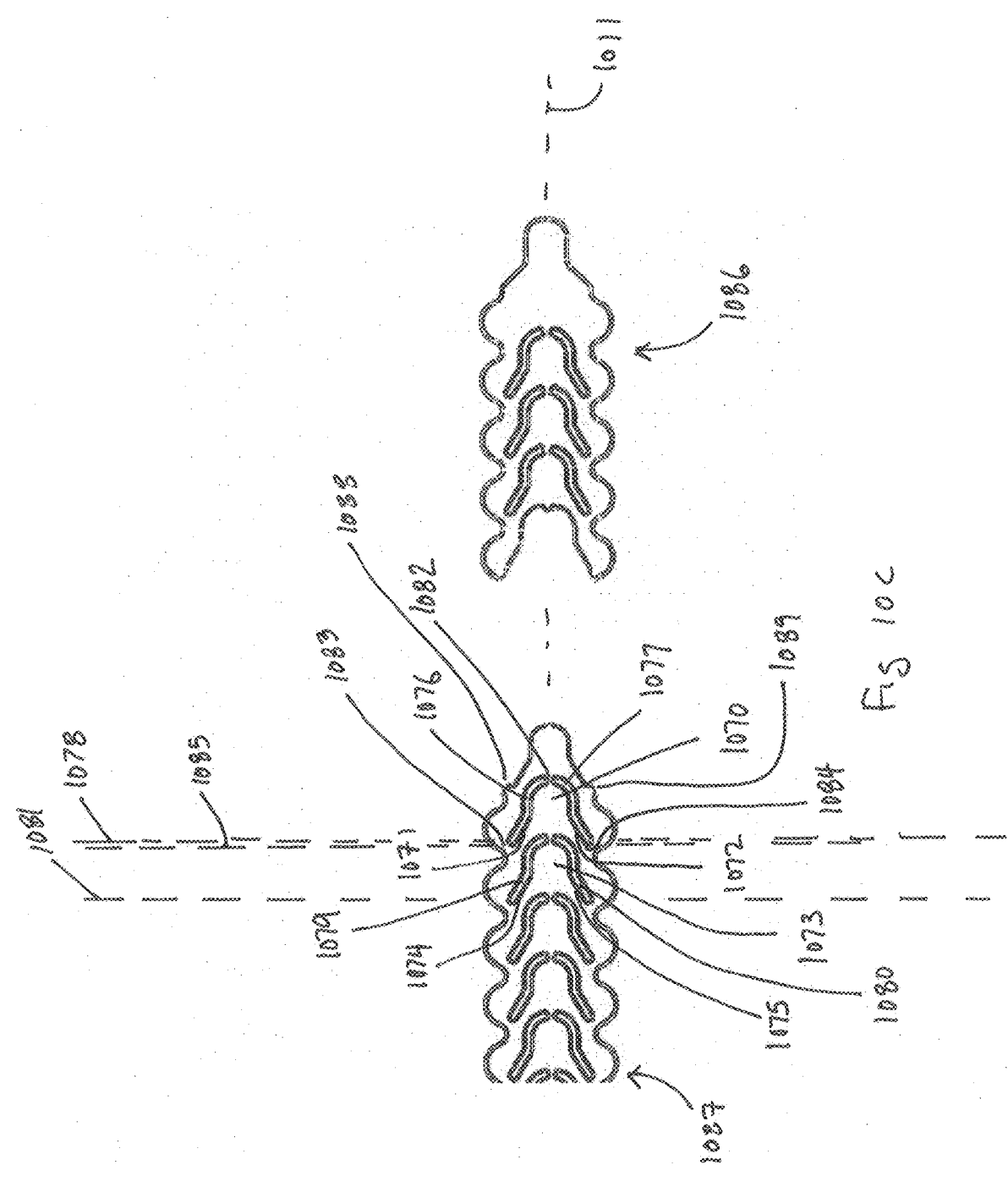
FIG. 10C shows an amplified view of the separated distal and proximal portions of the IV band.

While FIG. 10C does not show axis 1078 precisely intersecting the innermost core of portions 1083, 1084, axis 1078 may be moved to do so in various embodiments.

Some embodiments may include locations 1083, 1084 but exclude portion 1082.

In an embodiment, the first solid portion includes perforations to aid failure of the first solid portion and shortening of the band.

Example 6a. The IV securement band according to any of Examples 1a-4a, wherein: the first void is separated from the first sidewall by a first solid portion of the band; the second void is separated from the second sidewall by a second solid portion of the band; a third axis (1085), which is orthogonal to the long axis, intersects the first and second solid portions of the band.

Example 7a. The IV securement band according to any of Examples 1a-6a, wherein: the first and second solid portions of the band are configured to fail under a tension before the proximal third fails under the same tension; the band is configured so a distal subportion (1086) of the band is separable from a proximal subportion (1087) of the band in response to failure of the first and second solid portions of the band.

In FIG. 10C the distal subportion has separated from the proximal subportion by severing the band at areas 1088, 1089, which are analogous to areas 1083, 1084.

Example 8a. The IV securement band of Example 7a, wherein the tension is between 0 and 3 lbs. of force.

Example 9a. The IV securement band according to any of Examples 1a-8a, wherein the band is configured, based on at least the hardness of the resilient material and the second width being greater than the first width by a ratio not greater than 1.4, such that tightening the band by simultaneously advancing one of the first, second, and third protuberances and one of the fourth, fifth, and sixth protuberances through the slot requires between 1 and 4 pounds of force.

Such a ratio is critical in some embodiments for proper device function.

Another version of Example 9a. The IV securement band according to any of Examples 1a-8a, wherein the band is configured, based on at least the hardness of the resilient material, a shape of the protuberances, and the second width being greater than the first width by a ratio not greater than 1.4, such that the band automatically loosens to expand a loop formed by the band such that one or more of the protuberances slip though the slot when expansile force on the loop exceeds a predetermined limit.

As a result, if the band is tightened too much about a human body part, the band's loop may loosen to allow fluid flow through the body part and/or a conduit that is included in the loop.

In other embodiments, the ratio is between 1.1 and 1.5. By "between" 1.1 and 1.5 such values do not include 1.1 or 1.5.

Example 10a. The IV securement band of Example 9a, wherein simultaneously advancing the one of the first, second, and third protuberances and the one of the fourth, fifth, and sixth protuberances through the slot requires less force than the tension required for the first and second solid portions of the band to fail.

Example 11a. The IV securement band according to any of Examples 1a-10a, wherein: a distal tip of the band defines a distal tongue configured to pass through the slot; the first flap defines a first tongue configured to pass through the slot; the second flap defines a second tongue configured to pass through the slot.

Example 12a. The IV securement band of Example 11a, wherein the second flap is configured to be a distal most tongue in response to the distal tongue and the first tongue both being removed from the band via failure of the first and second solid portions of the band.

Example 12.1a The IV securement band according to any of Examples 1a-12a, wherein a minimal distance between the first void and the first sidewall is less than 0.1 inches.

As a result, the IV securement band has portions (e.g., area that has less than 0.1 inches wide) designed to fail when pulled manually with sufficient force. Such a dimension is critical in some embodiments for proper device function.

Example 13a. The IV securement band according to any of Examples 1a-12.1a, wherein the resilient material includes at least one of a thermoplastic elastomer, silicone, rubber, or combinations thereof.

Example 14a. The IV securement band according to any of Examples 1a-13a, wherein the resilient material has a hardness, the hardness being no softer than a Shore A 30 hardness and no harder than a Shore A 50 hardness.

Such a hardness is critical in some embodiments for proper device function.

Example 14.1a The IV securement band according to any of Examples 1a-14a, wherein a minimal distance between the first void and the first sidewall is less than 0.1 inches.

As a result, the band has portions (e.g., area that has less than 0.1 inches wide with sufficient softness) designed to fail when pulled manually with sufficient force. Such a dimension is critical in some embodiments for proper device function.

In other embodiments, the minimal distance of Example 14.1a is less than 0.09, 0.08, 0.07, 0.06, 0.05 inches. Such a distance may be critical to allow for manual adjustment to the length of the band.

Example 15a. The IV securement band according to any of Examples 1a-14a, wherein the second width is greater than the first width by a ratio no greater than 1.4.

Example 16a. The IV securement band of Example 15a, wherein: the ratio is between 1.1 and 1.2; the third width is wider than the second width by no less than 0.30 inches and no more than 0.40 inches.

Such a dimension is critical in some embodiments for proper device function.

Example 17a. The IV securement band according to any of Examples 1a-16a, wherein the second width is wider than the first width by no less than 0.10 inches and no more than 0.15 inches.

Example 18a. The IV securement band according to any of Examples 1a-17a, wherein (a) the first protuberance includes a leading edge that slopes away from the long axis as the leading edge extends proximally, (b) the first protuberance includes a trailing edge; and (c) the leading edge has a first angle of incidence with the first sidewall and the trailing edge has a second angle of incidence with the first sidewall.

Example 19a. The IV securement band according to Example 18a, wherein: the leading edge is longer than the trailing edge; and the first angle of incidence is less than the second angle of incidence.

Example 20a. The IV securement band according to Example 18a, wherein there is no negative space between any portion of the trailing edge and the tip of the first protuberance.

Example 21a. The IV securement band according to any of Examples 1a-20a, wherein an additional axis, which is orthogonal to the long axis, intersects the first sidewall and the tip of the first protuberance without traversing a void between the first sidewall and the tip of the first protuberance.

Example 22a. The IV securement band according to any of Examples 1a-21a, wherein the band is configured such that: tightening the band by simultaneously advancing the third and sixths protuberance through the slot takes more force than tightening the band by simultaneously advancing the first and fourth protuberances through the slot; the third protuberance is proximal to the first protuberance when the first face is substantially included in a plane; the sixth protuberance is proximal to the fourth protuberance when the first face is substantially included in the plane.

Example 23a. The IV securement band according to any of Examples 1a-22a, wherein the band is configured, based on at least the hardness of the resilient material and the second width being greater than the first width by a ratio not greater than 1.4, such that loosening the band by simultaneously withdrawing one of the first, second, and third protuberances and one of the fourth, fifth, and sixth protuberances through the slot requires between 1 and 4.0 pounds of force.

This may help the band to "auto loosen" and ensure fluid flow the IV tube is possible.

Example 23a. The IV securement band according to any of Examples 1a-22a, wherein the band is configured, based on at least the hardness of the resilient material and the second width being greater than the first width by a ratio not greater than 1.4, such that: loosening the band by simultaneously withdrawing the third and sixths protuberances through the slots takes more force than loosening the band by simultaneously withdrawing the first and fourth protuberances through the slot; the third protuberance is proximal to the first protuberance when the first face is substantially included in a plane; the sixth protuberance is proximal to the fourth protuberance when the first face is substantially included in the plane.

Example 31a. An IV securement band comprising: a substantially flat first face opposite a substantially flat second face; a first side wall opposite a second side wall, the first and second side walls coupling the first and second flat faces to each other; a distal portion of the first sidewall including first, second, and third protuberances, and a distal portion of the second sidewall including fourth, fifth, and sixth protuberances; a slot including a first width that is orthogonal to a long axis of the band; a second width, extending parallel to the first width and from the tip of the first protuberance to a tip of the fourth protuberance, which is greater than the first width by a ratio of the second width to the first width that is not greater than 1.4; a resilient material that has hardness not softer than a Shore A 30 hardness and not harder than a Shore A 50 hardness; a first flap (1070) having proximal portions (1071, 1072), the proximal portions of the first flap tapering outwardly away from the long axis (1011) and towards the first and second sidewalls as the proximal portions of the first flap extend proximally towards the slot; a second flap (1073) having proximal portions (1074, 1075), the proximal portions of the second flap tapering outwardly away from the long axis and towards the first and second sidewalls as the proximal portions of the second flap extend proximally towards the slot, the second flap being proximal to the first flap; first and second voids (1076, 1077) that are not contiguous with one another and which do not connect to either of the first or second sidewalls; wherein a first axis (1078), which is orthogonal to the long axis, intersects the first and second sidewalls, the proximal portions of the first flap, and the first and second voids; wherein (a) the first protuberance includes a leading edge that slopes away from a long axis of the band as the leading edge extends proximally, and (b) the first protuberance includes a trailing edge; wherein the band is monolithic and formed from a single structure with no fusions, welds, or adhesions between different sub-portions of the first band.

Example 32a. The IV securement band of Example 31a comprising third and fourth voids (1079, 1080) that are not contiguous with one another and which do not connect to either of the first or second sidewalls; wherein a second axis (1081), which is orthogonal to the long axis, intersects the first and second sidewalls, the proximal portions of the second flap, and the third and fourth voids.

Example 33a. The band of Example 32a, wherein the first axis intersects the third and fourth voids.

Example 34a. The IV securement band according to any of Examples 31a-33a, wherein: the first and second voids are separated from each other by a solid portion (1082) of the band; the long axis intersects the solid portion of the band.

Example 35a. The IV securement band according to any of Examples 31a-34a, wherein: the first void is separated from the first sidewall by a first solid portion (1083) of the band; the second void is separated from the second sidewall by a second solid portion (1084) of the band; the first axis intersects the first and second solid portions of the band.

While FIG. 10C does not show axis 1078 precisely intersecting the innermost core of portions 1083, 1084, axis 1078 may be moved to do so in various embodiments.

Example 36a. The IV securement band according to any of Examples 31a-34a, wherein: the first void is separated from the first sidewall by a first solid portion of the band; the second void is separated from the second sidewall by a second solid portion of the band; a third axis (1085), which is orthogonal to the long axis, intersects the first and second solid portions of the band.

Example 37a. The IV securement band according to any of Examples 31a-36a, wherein: the first and second solid portions of the band are configured to fail under tension before the proximal third fails under the same tension; the band is configured so a distal subportion (1086) of the band is separable from a proximal subportion (1087) of the band in response to failure of the first and second solid portions of the band.

In FIG. 10C the distal subportion has separated from the proximal subportion by severing the band at areas 1088, 1089, which are analogous to areas 1083, 1084.

Example 38a. The IV securement band of Example 37a, wherein the tension is between 0 and 3 lbs. of force.

Example 39a. The IV securement band according to any of Examples 31a-38a, wherein the band is configured, based on at least the hardness of the resilient material and the second width being greater than the first width by a ratio not greater than 1.4, such that tightening the band by simultaneously advancing one of the first, second, and third protuberances and one of the fourth, fifth, and sixth protuberances through the slot requires between 1 and 4 pounds of force.

Example 40a. The IV securement band of Example 39a, wherein simultaneously advancing the one of the first, second, and third protuberances and the one of the fourth, fifth, and sixth protuberances through the slot requires less force than the tension required for the first and second solid portions of the band to fail.

Example 41a. The IV securement band according to any of Examples 31a-40a, wherein: a distal tip of the band defines a distal tongue configured to pass through the slot; the first flap defines a first tongue configured to pass through the slot; the second flap defines a second tongue configured to pass through the slot.

Example 42a. The IV securement band of Example 41a, wherein the second flap is configured to be a distal most tongue in response to the distal tongue and the first tongue both being removed from the band via failure of the first and second solid portions of the band.

Example 43a. The IV securement band according to any of Examples 31a-42a, wherein the resilient material includes at least one of a thermoplastic elastomer, silicone, rubber, or combinations thereof.

Example 44a. The IV securement band according to any of Examples 31a-43a, wherein the resilient material has a hardness, the hardness being no softer than a Shore A 30 hardness and no harder than a Shore A 50 hardness.

Example 45a. The IV securement band according to any of Examples 31a-44a, wherein the second width is greater than the first width by a ratio not greater than 1.4.

Example 46a. The IV securement band of Example 45a, wherein: the ratio is between 1.1 and 1.2; the third width is wider than the second width by no less than 0.30 inches and no more than 0.40 inches.

Example 47a. The IV securement band according to any of Examples 31a-46a, wherein the second width is wider than the first width by no less than 0.10 inches and no more than 0.15 inches.

Example 48a. The IV securement band according to any of Examples 31a-47, wherein (a) the first protuberance includes a leading edge that slopes away from the long axis as the leading edge extends proximally, (b) the first protuberance includes a trailing edge; and (c) the leading edge has a first angle of incidence with the first sidewall and the trailing edge has a second angle of incidence with the first sidewall.

Example 49a. The IV securement band according to Example 48a, wherein: the leading edge is longer than the trailing edge; and the first angle of incidence is less than the second angle of incidence.

Example 50a. A method comprising forming a loop by sliding the first protuberance of the IV securement band according to any of examples 1a through 49a through the slot to form a loop with the IV securement band and affix the IV securement band to an object located within the loop.

Another version of Example 50a. A method comprising forming a loop by sliding the first protuberance of the IV securement band according to any of examples 31a through 49a through the slot to form a loop with the IV securement band and affix the IV securement band to an object located within the loop.

Example 51a. The method of Example 50a comprising adjusting an overall length of the IV securement band by tearing or severing the IV securement band at any of locations 1082, 1083, 1084.

In an embodiment, FIG. 11 provides example dimensions that may cooperate with each other to help form a band that automatically loosens when fastened too tightly about an object. In addition, the dimensions may cooperate with each other so that a first tension on the distal end of the band may help tighten the band about an object but a greater force will actually separate one or more distal flaps from a proximal portion of the band. The separation may occur before or after a loop is made with the band.

Some embodiments may have only one or two of locations analogous to locations 1082, 1083, 1084. However, other embodiments may have 4 or more of such locations that are configured, through thickness and/or material qualities, to fail when pulled manually with less than 3 pounds of force.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a device side (or active surface) of a substrate or integrated circuit is the "top" surface of that substrate; the substrate may actually be in any orientation so that a "top" side of a substrate may be lower than the "bottom" side in a standard terrestrial frame of reference and still fall within the meaning of the term "top." The term "on" as used herein (including in the claims) does not indicate that a first layer "on" a second layer is directly on and in immediate contact with the second layer unless such is specifically stated; there may be a third layer or other structure between the first layer and the second layer on the first layer. The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

What is claimed is:

1. An intravenous (IV) securement band comprising:

an overall length defined along a long axis of the band;

a proximal third, a distal third, and a middle third between the proximal and distal thirds;

a substantially flat first face opposite a substantially flat second face;

a first sidewall opposite a second sidewall, the first sidewall coupling the first and second flat faces to each other and the second sidewall also coupling the first and second flat faces to each other;

a distal portion of the first sidewall, the distal portion of the first sidewall including first, second, and third protuberances, and a distal portion of the second sidewall, the distal portion of the second sidewall including fourth, fifth, and sixth protuberances;

a proximal portion of the first sidewall, the proximal portion of the first sidewall including no protuberances, and a proximal portion of the second sidewall, the proximal portion of the second sidewall including no protuberances;

a tip of the first protuberance that extends a first distance, orthogonal to the long axis, from the long axis; wherein the proximal portion of the first sidewall extends a second distance, orthogonal the long axis, from the long axis and the first distance is greater than the second distance;

a slot included in the proximal third of the band and including a first width that is orthogonal to the long axis;

a second width extending orthogonal to the long axis and from the tip of the first protuberance to a tip of the fourth protuberance, wherein the second width is wider than the first width;

a third width colinear with the first width and extending from the first sidewall to the second sidewall, wherein the third width is wider than the second width;

a resilient material;

a first flap having proximal portions, the proximal portions of the first flap tapering outwardly away from the long axis and towards the first and second sidewalls as the proximal portions of the first flap extend proximally towards the slot;

a second flap having proximal portions, the proximal portions of the second flap tapering outwardly away from the long axis and towards the first and second sidewalls as the proximal portions of the second flap extend proximally towards the slot, the second flap being proximal to the first flap;

first and second voids that are not contiguous with one another and which do not connect to either of the first or second sidewalls;

wherein a first axis, which is orthogonal to the long axis, intersects the first and second sidewalls, the proximal portions of the first flap, and the first and second voids;

wherein the band is monolithic and formed from a single structure with no fusions, welds, or adhesions between different sub-portions of the band.

2. The IV securement band of claim 1, comprising third and fourth voids that are not contiguous with one another and which do not connect to either of the first or second sidewalls;

wherein a second axis, which is orthogonal to the long axis, intersects the first and second sidewalls, the proximal portions of the second flap, and the third and fourth voids.

3. The IV securement band of claim 2, wherein the first axis intersects the third and fourth voids.

4. The IV securement band of claim 2, wherein:

the first and second voids are separated from each other by a solid portion of the band;

the long axis intersects the solid portion of the band.

5. The IV securement band of claim 2, wherein:

the first void is separated from the first sidewall by a first solid portion of the band;

the second void is separated from the second sidewall by a second solid portion of the band;

the first axis intersects the first and second solid portions of the band.

6. The IV securement band of claim 2, wherein:

the first void is separated from the first sidewall by a first solid portion of the band;

the second void is separated from the second sidewall by a second solid portion of the band;

a third axis, which is orthogonal to the long axis, intersects the first and second solid portions of the band.

7. The IV securement band of claim 6, wherein:

the first and second solid portions of the band are configured to fail under a tension before the proximal third fails under the same tension;

the band is configured so a distal subportion of the band is separable from a proximal subportion of the band in response to failure of the first and second solid portions of the band.

8. The IV securement band of claim 7, wherein the tension is between 0 and 3 lbs of force.

9. The IV securement band of claim 1, wherein the band is configured, based on at least a hardness of the resilient material and the second width being greater than the first width by a ratio not greater than 1.4, such that tightening the band by simultaneously advancing one of the first, second, and third protuberances and one of the fourth, fifth, and sixth protuberances through the slot requires between 1 and 4 pounds of force.

10. The IV securement band of claim 1, wherein the band is configured, based on at least a hardness of the resilient material, a shape of any one or more of the first, second, and third protuberances, and the second width being greater than the first width by a ratio not greater than 1.4, such that the band automatically loosens to expand a loop formed by the band such that one or more of the first, second, and third protuberances slip though the slot when expansile force on the loop exceeds a predetermined limit.

11. The IV securement band of claim 6, wherein:

a distal tip of the band defines a distal tongue configured to pass through the slot;

the first flap defines a first tongue configured to pass through the slot;

the second flap defines a second tongue configured to pass through the slot.

12. The IV securement band of claim 11, wherein the second flap is configured to be a distal most tongue in response to the distal tongue and the first tongue both being removed from the band via failure of the first and second solid portions of the band.

13. The IV securement band of claim 1, wherein the resilient material has a hardness, the hardness being no softer than a Shore A 30 hardness and no harder than a Shore A 50 hardness.

14. The IV securement band of claim 13, wherein a distance between the first void and the first sidewall is less than 0.1 inches.

15. The IV securement band of claim 14, wherein the second width is greater than the first width by a ratio no greater than 1.4.

16. The IV securement band of claim 15, wherein:

the ratio is between 1.1 and 1.2;

the third width is wider than the second width by no less than 0.30 inches and no more than 0.40 inches;

the second width is wider than the first width by no less than 0.10 inches and no more than 0.15 inches.

17. The IV securement band of claim 1, wherein the band is configured, based on at least a hardness of the resilient material and the second width being greater than the first width by a ratio not greater than 1.4, such that loosening the band by simultaneously withdrawing one of the first, second, and third protuberances and one of the fourth, fifth, and sixth protuberances through the slot requires between 1 and 4.0 pounds of force.

18. An IV securement band comprising:

a substantially flat first face opposite a substantially flat second face;

a first sidewall opposite a second sidewall, the first and second sidewalls coupling the first and second flat faces to each other;

a distal portion of the first sidewall including first, second, and third protuberances, and a distal portion of the second sidewall including fourth, fifth, and sixth protuberances;

a slot including a first width that is orthogonal to a long axis of the band;

a second width, extending parallel to the first width and from a tip of the first protuberance to a tip of the fourth protuberance, which is greater than the first width by a ratio of the second width to the first width that is not greater than 1.4;

a resilient material that has a hardness not softer than a Shore A 30 hardness and not harder than a Shore A 50 hardness;

a first flap having proximal portions, the proximal portions of the first flap tapering outwardly away from the long axis and towards the first and second sidewalls as the proximal portions of the first flap extend proximally towards the slot;

a second flap having proximal portions, the proximal portions of the second flap tapering outwardly away from the long axis and towards the first and second sidewalls as the proximal portions of the second flap extend proximally towards the slot, the second flap being proximal to the first flap;

first and second voids that are not contiguous with one another and which do not connect to either of the first or second sidewalls;

wherein a first axis, which is orthogonal to the long axis, intersects the first and second sidewalls, the proximal portions of the first flap, and the first and second voids;

wherein (a) the first protuberance includes a leading edge that slopes away from a long axis of the band as the leading edge extends proximally, and (b) the first protuberance includes a trailing edge;

wherein the band is monolithic and formed from a single structure with no fusions, welds, or adhesions between different sub-portions of the fir-t band.

19. The IV securement band of claim 18 comprising third and fourth voids that are not contiguous with one another and which do not connect to either of the first or second sidewalls; wherein the first axis intersects the third and fourth voids.

20. The IV securement band of claim 18, wherein:

the first void is separated from the first sidewall by a first solid portion of the band;

the second void is separated from the second sidewall by a second solid portion of the band;

the first and second solid portions of the band are configured to fail under a tension before a proximal third of the band fails under the same tension;

the band is configured so a distal subportion of the band is separable from a proximal subportion of the band in response to failure of the first and second solid portions of the band;

the tension is between 0 and 3 lbs of force.

\* \* \* \* \*